United States Patent
Shiomi et al.

(10) Patent No.: US 9,450,194 B2
(45) Date of Patent: Sep. 20, 2016

(54) HETEROARENE DERIVATIVE AND ORGANIC ELECTROLUMINESCENCE DEVICE USING THE SAME

(71) Applicant: Idemitsu Kosan Co., Ltd., Tokyo (JP)

(72) Inventors: Takushi Shiomi, Sodegaura (JP); Kazuki Nishimura, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 347 days.

(21) Appl. No.: 14/142,119

(22) Filed: Dec. 27, 2013

(65) Prior Publication Data

US 2014/0183504 A1   Jul. 3, 2014

(30) Foreign Application Priority Data

Dec. 28, 2012 (JP) .................................. 2012-286659

(51) Int. Cl.
*H01L 51/00* (2006.01)
*C07F 5/02* (2006.01)
*H01L 51/50* (2006.01)

(52) U.S. Cl.
CPC ............... *H01L 51/008* (2013.01); *C07F 5/02* (2013.01); *H01L 51/0072* (2013.01); *H01L 51/5012* (2013.01); *H01L 51/5016* (2013.01)

(58) Field of Classification Search
None
See application file for complete search history.

(56) References Cited

FOREIGN PATENT DOCUMENTS

JP          2011184430 A  *  9/2011
WO      WO-2011/099331 A1     8/2011

OTHER PUBLICATIONS

Machine English translation of JP 2011-184430 A. Feb. 4, 2016.*

* cited by examiner

*Primary Examiner* — J. L. Yang
(74) *Attorney, Agent, or Firm* — Foley & Lardner LLP

(57) ABSTRACT

A heteroarene derivative including a nitrogen-boron coordinate bond, represented by the following formula (1). In the formula (1), $Z_1$ is a group represented by the following formula (2); $Z_2$ is a substituted or unsubstituted aryl group including 6 to 30 ring carbon atoms or a substituted or unsubstituted heteroaryl group including 5 to 30 ring atoms; L is a substituted or unsubstituted arylene including 6 to 30 ring carbon atoms, a substituted or unsubstituted heteroarylene including 5 to 30 ring atoms, —O—, —S—, —($CR_2R_3$)$_n$— (wherein n is an integer of 1 to 8).

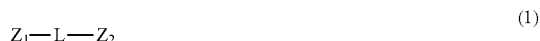

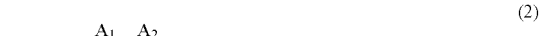

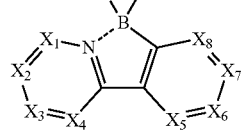

6 Claims, No Drawings

HETEROARENE DERIVATIVE AND ORGANIC ELECTROLUMINESCENCE DEVICE USING THE SAME

TECHNICAL

The invention relates to a heteroarene derivative comprising a nitrogen-boron coordinate bond and a material for an organic electroluminescence using the same.

BACKGROUND ART

A material for an organic electroluminescence device that is capable of improving the performance of an organic electroluminescence device has conventionally been required. For example, as an electron-injecting/transporting group, an electron-deficient heteroaryl group, such as pyridine, pyrimidine and triazine, is known.

In Patent Document 1, as a material for a functional electronic device, a compound having the following structure, or the like is disclosed; specifically a structure in which a group formed by coordination of a boron atom to a heteroaryl group is sandwiched by two carbazolyl groups. The luminous quantum efficiency thereof is measured.

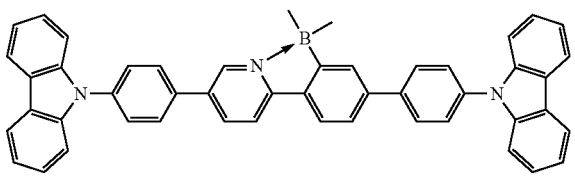 [SMILES: C[B-]1(C)c2cc(-c3ccc(-n4c5ccccc5c5ccccc54)cc3)ccc2-c2ccc(-c3ccc(-n4c5ccccc5c5ccccc54)cc3)c[n+]21]

RELATED ART DOCUMENTS

Patent Documents

Patent Document 1: WO2011/099331

SUMMARY OF THE INVENTION

The invention is aimed at providing a novel heteroarene derivative and a material for an organic electroluminescence device comprising the heteroarene derivative.

According to the invention, the heteroarene derivative comprising the following nitrogen-boron coordinate bond, or the like are provided.

1. A heteroarene derivative comprising a nitrogen-boron coordinate bond, represented by the following formula (1):

$$Z_1\text{-}L\text{-}Z_2 \quad (1)$$

wherein in the formula (1), $Z_1$ is a group represented by the following formula (2);

$Z_2$ is a substituted or unsubstituted aryl group including 6 to 30 carbon atoms that form a ring (hereinafter referred to as "ring carbon atoms") or a substituted or unsubstituted heteroaryl group including 5 to 30 atoms that form a ring (hereinafter referred to as "ring atoms");

L is a substituted or unsubstituted arylene including 6 to 30 ring carbon atoms, a substituted or unsubstituted heteroarylene including 5 to 30 ring atoms, —O—, —S—, —(CR$_2$R$_3$)$_n$— (wherein n is an integer of 1 to 8, and R$_2$ and R$_3$ are independently a substituted or unsubstituted alkyl group including 1 to 30 carbon atoms, a substituted or unsubstituted aryl group including 6 to 30 ring carbon atoms or a substituted or unsubstituted heteroaryl group including 5 to 30 ring atoms) or a single bond;

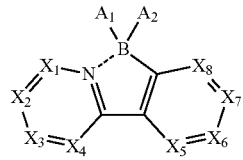

wherein in the formula (2), $X_1$ to $X_8$ are independently N (nitrogen atom) or $CR_1$ (C is a carbon atom);

$R_1$ is a single bond, a hydrogen atom or a substituent, and if plural $R_1$s are present, the plural $R_1$s may be the same or different;

one of $X_1$ to $X_8$ is $CR_1$ in which $R_1$ is a single bond and $R_1$ is bonded to L, provided that, if L is a single bond, $R_1$ is bonded directly to $Z_2$;

and if the remainder of $X_1$ to $X_8$ is independently $CR_1$, $R_1$ is not the same as -L-$Z_2$;

A1 and A2 are independently a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted alkoxy group including 1 to 30 carbon atoms, a substituted or unsubstituted aryloxy group including 6 to 30 ring carbon atoms, a substituted or unsubstituted alkylamino group including 1 to 30 carbon atoms, a substituted or unsubstituted arylamino group including 6 to 30 ring carbon atoms or a halogen atom; and a broken line between B and N is a coordinate bond.

2. The heteroarene derivative according to 1, wherein Z2 is carbazolyl, dibenzofuranyl, dibenzothiophenyl, fluorenyl, dibenzosilolyl, triphenylenyl, benzoimidazolyl, indolyl, benzofuranyl, benzothiophenyl, benzosilolyl, pyrimidinyl, triazinyl, quinolinyl, quinazolinyl, phenanthrolynyl, naphthyl, anthracenyl, phenanthryl, chrysenyl, pyrenyl, fluoranthenyl, phenoxazinyl, phenothiazinyl, phenoxathiinyl, a monovalent group of the following formula (3) (R4, R5 and R6 are independently a substituted or unsubstituted alkyl group including 1 to 30 carbon atoms, a substituted or unsubstituted aryl group including 6 to 30 ring carbon atoms or a substituted or unsubstituted heteroaryl group including 5 to 30 ring atoms, or one of R4, R5 and R6 is a single bond that is bonded to L), a monovalent group of the following formula (4) or a heteroaryl group obtained by substituting one or more of the carbon atoms forming a ring of these groups by a nitrogen atom (provided that the carbon atom at the ring-bonding site is not substituted by a nitrogen atom).

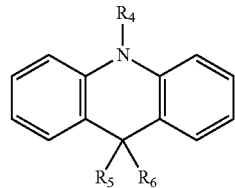

-continued (4)

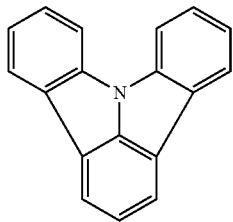

3. The heteroarene derivative according to 1, wherein $Z_2$ is a group represented by the following formula (5):

(5)

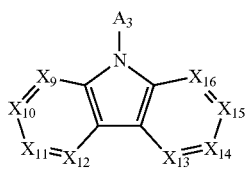

wherein in the formula (5), $X_9$ to $X_{16}$ are independently N (nitrogen atom) or $CR_7$ (C is a carbon atom);

$R_7$ is a single bond, a hydrogen atom or a substituent, and if plural $R_7$s are present, the plural $R_7$s may be the same or different;

$A_3$ is a single bond or a substituent; and one of $R_7$s or $A_3$ is a single bond that is bonded to L, provided that if L is a single bond, one of $R_7$s or $A_3$ is directly bonded to $Z_1$.

4. The heteroarene derivative according to 1, wherein $Z_2$ is a group represented by the following formula (6) or (7):

(6)

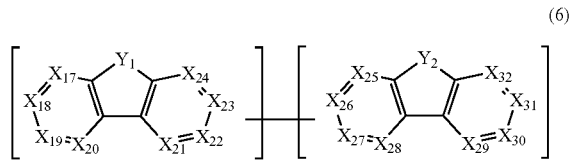

wherein in the formula (6), $X_{17}$ to $X_{32}$ are independently N (nitrogen atom) or $CR_8$ (C is a carbon atom);

$R_8$ is a single bond, a hydrogen atom or a substituent; and if plural $R_8$s are present, the plural $R_8$s may be the same or different;

$Y_1$ and $Y_2$ are independently $NR_9$, O, S, $CR_{10}R_{11}$ or $SiR_{12}R_{13}$, and $R_9$, $R_{10}$, $R_{11}$, $R_{12}$ and $R_{13}$, that may be the same or different, are a single bond, a substituted or unsubstituted alkyl group including 1 to 30 carbon atoms, a substituted or unsubstituted aryl group including 6 to 30 ring carbon atoms or a substituted or unsubstituted heteroaryl group including 5 to 30 ring atoms;

one of $R_8$ to $R_{13}$ is a single bond and is bonded to L, provided that if L is a single bond, one of $R_8$ to $R_{13}$ is directly bonded to $Z_1$;

(7)

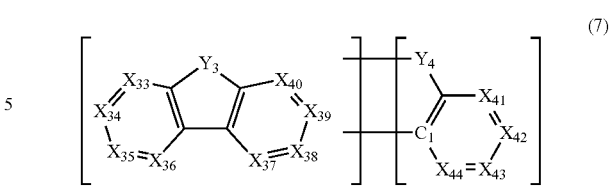

wherein in the formula (7), $X_{33}$ to $X_{44}$ are independently N (nitrogen atom) or $CR_{14}$ (C is a carbon atom);

$R_{14}$ is a single bond, a hydrogen atom or a substituent, and if plural $R_{14}$s are present, the plural $R_{14}$s may be the same or different;

$Y_3$ and $Y_4$ are independently $NR_{15}$, O, S, $CR_{16}R_{17}$ or $SiR_{18}R_{16}$; $R_{15}$, $R_{16}$, $R_{17}$, $R_{18}$ and $R_{19}$, that may be the same or different, are a single bond, a substituted or unsubstituted alkyl group including 1 to 30 carbon atoms, a substituted or unsubstituted aryl group including 6 to 30 ring carbon atoms or a substituted or unsubstituted heteroaryl group including 5 to 30 ring atoms;

$C_1$ is a carbon atom;

provided that, at least two of $X_{37}$ to $X_{40}$, being adjacent with each other, are both carbon atoms, and one of the two carbon atoms is bonded to $Y_4$ and the other is bonded to $C_1$; and one of $R_{14}$ to $R_{19}$ is a single bond and is bonded to L, provided that if L is a single bond, one of $R_{14}$ to $R_{19}$ is directly bonded to $Z_1$.

5. The heteroarene derivative according to any of 1 to 4, wherein $A_1$ and $A_2$ are independently a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted alkoxy group including 1 to 30 carbon atoms, a substituted or unsubstituted aryloxy group including 6 to 30 ring carbon atoms, a substituted or unsubstituted alkylamino group including 1 to 30 carbon atoms or a substituted or unsubstituted arylamino group including 6 to 30 ring carbon atoms.

6. The heteroarene derivative according to 1 to 5, wherein $A_1$ is a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted alkoxy group including 1 to 30 carbon atoms, a substituted or unsubstituted aryloxy group including 6 to 30 ring carbon atoms, a substituted or unsubstituted alkylamino group including 1 to 30 carbon atoms, a substituted or unsubstituted arylamino group including 6 to 30 ring carbon atoms or a halogen atom.

7. A material for an organic electroluminescence device comprising the heteroarene derivative according to any of 1 to 6.

8. An organic electroluminescence device comprising a cathode and an anode and one or more organic thin film layers including an emitting layer between the cathode and the anode, wherein at least one of the organic thin film layers comprises the material for an organic electroluminescence device according to 7.

9. The organic electroluminescence device according to 8, wherein the emitting layer comprises the material for an organic electroluminescence device.

According to the invention, a novel heteroarene derivative and a material for an organic electroluminescence device comprising the heteroarene derivative can be provided.

MODE FOR CARRYING OUT THE INVENTION

The heteroarene derivative according to the invention that comprises a nitrogen-boron coordinate bond is represented by the following formula (1):

$$Z_1\text{-}L\text{-}Z_2 \quad (1)$$

wherein in the formula (1). $Z_1$ is a group represented by the following formula (2);

$Z_2$ is a substituted or unsubstituted aryl group including 6 to 30 carbon atoms that form a ring (hereinafter referred to as the "ring carbon atoms") or a substituted or unsubstituted heteroaryl group including 5 to 30 atoms that form a ring (hereinafter referred to as the "ring atoms");

L is a substituted or unsubstituted arylene including 6 to 30 ring carbon atoms, a substituted or unsubstituted heteroarylene including 5 to 30 ring atoms, —O—, —S—, —(CR$_2$R$_3$)$_n$— (wherein n is an integer of 1 to 8. R$_2$ and R$_3$ are independently a substituted or unsubstituted alkyl group including 1 to 30 carbon atoms, a substituted or unsubstituted aryl group including 6 to 30 ring carbon atoms, or a substituted or unsubstituted heteroaryl group including 5 to 30 ring atoms) or a single bond.

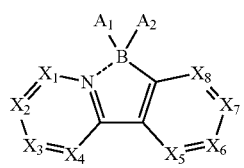

(2)

wherein in the formula (2), $X_1$ to $X_8$ are independently N (nitrogen atom) or CR$_1$ (C is a carbon atom);

R$_1$ is a single bond, a hydrogen atom or a substituent, and if plural R$_1$s are present, the plural R$_1$s may be the same or different;

one of $X_1$ to $X_8$ is CR$_1$ in which R$_1$ is a single bond and R$_1$ is bonded to L, provided that, if L is a single bond. R$_1$ is bonded directly to $Z_2$;

and if the remainder of $X_1$ to $X_8$ is independently CR$_1$, R$_1$ is not the same as -L-Z$_2$;

A$_1$ and A$_2$ are independently a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted alkoxy group including 1 to 30 carbon atoms, a substituted or unsubstituted aryloxy group including 6 to 30 ring carbon atoms, a substituted or unsubstituted alkylamino group including 1 to 30 carbon atoms, a substituted or unsubstituted arylamino group including 6 to 30 ring carbon atoms or a halogen atom; and a broken line between B and N is a coordinate bond.

In the case where $X_1$ to $X_8$ are CR$_1$, two R$_1$s may form a ring. In the case where $X_1$ and $X_8$ are CR$_1$, A$_1$ and $X_1$, and A$_2$ and $X_8$ may respectively form a ring.

In the case where L is a single bond, by bonding to any one of A$_1$ and A$_2$ and $X_1$ to $X_8$ in the group $Z_1$ represented by the formula (2), other than the single bond of L, the aryl group and the heteroaryl group represented by $Z_2$ may be an aryl group or a heteroaryl group that shares part of the ring represented by the formula (2).

As the electron-injecting/transporting group, an electron-deficient heteroaryl group such as pyridine, pyrimidine and triazine has heretofore been known. By allowing pyridine, pyrimidine, triazine or the like to be further electron deficient, it is expected that they become a skeleton having a further excellent electron-injecting/transporting properties. Normally, utilization of resonance effects or induction effects by an electron-attracting group can be considered as a method for attaining electron deficiency.

On the other hand, in the invention, the derivative is allowed to be electron deficient by coordinating a boron atom to a nitrogen atom of pyridine, pyrimidine, triazine or the like. By utilizing flowing in of electrons to the unoccupied orbital of a boron atom from a lone pair of a nitrogen atom, it is possible to allow the heteroaryl group to be further electron deficient. Specifically, a heteroarene derivative comprising group $Z_1$ in which a boron atom is coordinated to a heteroaryl group as an electron-injecting/transporting group is provided.

Hereinbelow, a detailed explanation will be made on each group in the formula (1).

As the aryl group including 6 to 30 (preferably 6 to 14) ring carbon atoms in $Z_2$, L, A$_1$ and A$_2$, a non-fused aryl group and a fused aryl group can be given. More specific examples thereof include a phenyl group, a naphthyl group, an anthracenyl group, a phenanthryl group, a pyrenyl group, a chrysenyl group, a biphenyl group, a terphenyl group, a quarterphenyl group, a fluoranthenyl group, a triphenylenyl group, a fluorenyl group, a spirofluorenyl group, a 9,9-diphenylfluorenyl group, a 9,9'-spirobi[9H-fluorene]-2-yl group (spirobifluorenyl group), a 9,9-dimethylfluorenyl group, a benzo[c]phenanthrenyl group, a benzo[a]triphenylenyl group, a naphtho[1,2-c]phenanthrenyl group, a naphtho[1,2-a]triphenylenyl group, a dibenzo[a,c]triphenylenyl group, a benzo[b]fluoranthenyl group or the like. Among them, a phenyl group, a naphthyl group, a phenanthryl group, a biphenyl group, a terphenyl group, a fluoranthenyl group, a triphenylenyl group, a fluorenyl group and a spirobifluorenyl group are preferable.

As the heteroaryl group including 5 to 30 (preferably 5 to 14) ring atoms in $Z_2$, L, A$_1$ and A$_2$, a non-fused heteroaryl group and a fused heteroaryl group can be given. More specific examples thereof include a pyrrole ring, an isoindole ring, a benzofuran ring, an isobenzofuran ring, a benzothiophene ring, a dibenzothiophene ring, a benzosilole ring, a dibenzosilole ring, an isoquinoline ring, a quinoxaline ring, a phenanthridine ring, a phenanthroline ring, a phenoxazine ring, a phenothiazine ring, a phenoxathiin ring, a pyridine ring, a pyrazine ring, a pyrimidine ring, a pyridazine ring, a triazine ring, an indole ring, a quinoline ring, an acridine ring, a pyrrolidine ring, a dioxane ring, a piperidine ring, a morpholine ring, a piperazine ring, a furan ring, a thiophene ring, quinazoline ring, a carbazole ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, a benzo[c]dibenzofuran ring, a group formed from derivatives thereof, or the like. A dibenzofuran ring, a dibenzothiophene ring and a group formed from these derivatives are preferable.

As examples of the alkyl group including 1 to 30 (preferably 1 to 6) carbon atoms in A$_1$ and A$_2$, a methyl group, an ethyl group, an n-propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a cyclopropyl group, a cyclobutyl group, a cyclopentyl group, a cyclohexyl group, a cyclooctyl group, an adamantyl group and the like can be given. A methyl group, an ethyl group, an n-propyl group, an isopropyl group, an n-butyl group, an s-butyl group, an isobutyl group, a t-butyl group, a cyclopentyl group and a cyclohexyl group are preferable.

As the alkyl group including 1 to 30 (preferably 1 to 6) carbon atoms in $A_1$ and $A_2$, one obtained by substituting one hydrogen atom of the alkyl group including 1 to 30 carbon atoms by an —O— group can be given. Specifically, a methoxy group, an ethoxy group, a propoxy group, a pentyloxy group, a hexyloxy group or the like can be given.

As the aryloxy group including 6 to 30 (preferably 6 to 14) ring carbon atoms in $A_1$ and $A_2$, one obtained by substituting one hydrogen atom of the aryl group including 6 to 30 carbon atoms by an —O— group can be given.

As the alkylamino group including 1 to 30 (preferably 1 to 6) carbon atoms in $A_1$ and $A_2$, one obtained by bonding of the alkyl group including 1 to 30 carbon atoms to an amino group can be given.

As the arylamino group including 6 to 30 (preferably 6 to 14) ring carbon atoms in $A_1$ and $A_2$, one obtained by bonding of the aryl group including 6 to 30 carbon atoms to an amino group can be given.

As the halogen atom in $A_1$ and $A_2$, fluorine, chlorine, bromine, iodine or the like can be given, with fluorine being preferable.

As substituent when referring to the "substituent" or the arbitral substituent when referring to the "substituted or unsubstituted", a halogen atom (fluorine, chlorine, bromine, iodine), a cyano group, an alkyl group including 1 to 20 (preferably 1 to 6) carbon atoms, a cycloalkyl group including 3 to 20 (preferably 5 to 12) carbon atoms, an alkoxy group including 1 to 20 (preferably 1 to 5) carbon atoms, a haloalkyl group including 1 to 20 (preferably 1 to 5) carbon atoms, a haloalkoxy group including 1 to 20 (preferably 1 to 5) carbon atoms, an alkylsilyl group including 1 to 10 (preferably 1 to 5) carbon atoms, an aryl group (aromatic hydrocarbon group) including 6 to 30 (preferably 6 to 18) ring carbon atoms, an aryloxy group including 6 to 30 (preferably 6 to 18) carbon atoms, an arylsilyl group including 6 to 30 (preferably 6 to 18) ring carbon atoms, an aralkyl group including 7 to 30 (preferably 7 to 20) carbon atoms, a heteroaryl group (heterocyclic group) including 5 to 30 (preferably 5 to 18) ring atoms, an alkylamino group including 1 to 30 (preferably 1 to 6) carbon atoms and an arylamino group including 6 to 30 (preferably 6 to 14) ring carbon atoms can be given. These substituents may be further substituted by the arbitral substituent mentioned above.

As the alkyl group, the aryl group, the heteroaryl group, the aryloxy group, the alkylamino group and the arylamino group as the examples of the above-mentioned arbitral substituent, those mentioned above can be given.

As the cycloalkyl group, one in which the example of the alkyl group including 3 or more carbon atoms has an aliphatic ring structure can be given.

As the alkoxy group, a methoxy group, an ethoxy group, a propoxy group, a pentyloxy group, a hexyloxy group or the like can be given.

As the haloalkyl group, one obtained by substituting one or more hydrogen atoms by a halogen atom can be given. As the halogen atom, fluorine is preferable. A trifluoromethyl group, a 2,2-trifluoroethyl group or the like can be given.

As the haloalkoxy group, one obtained by substituting one or more hydrogen atoms in the alkoxy group by a halogen atom can be given. As the halogen atom, fluorine is preferable.

As the aralkyl group, one obtained by substituting one hydrogen atom of the non-fused aryl group and the fused aryl group by an alkyl group can be given.

As the alkylsilyl group, a trimethylsilyl group, a triethylsilyl group, a tributylsilyl group, a dimethylethylsilyl group, a t-butyldimethylsilyl group, a vinyldimethylsilyl group, a propyldimethylsilyl group, a dimethylisopropylsilyl group, a dimethylpropylsilyl group, a dimethylbutylsilyl group, a dimethyl tert-butylsilyl group, a diethylisopropylsilyl group, a phenyldimethylsilyl group, a diphenylmethylsilyl group, a diphenyl tert-butylsilyl group, a triphenylsilyl group, and the like.

As the arylsilyl group, one in which the alkyl portion of the alkylsilyl group is substituted by the aryl group can be given.

If $Z_2$ in the formula (1) is a carbazolyl group and $X_1$ to $X_8$ of $Z_1$ represented by the formula (2) is $CR_1$, it is preferred that $R_1$ as the substituent be not a carbazolyl group. This can suppress effects exerted by the electron-injecting/transporting group on hole injection and transportation and effects exerted by the hole-injecting/transporting group on electron injection and transportation by allowing the number of bonding sites between the electron-injecting/transporting group ($Z_1$ in which a boron atom is coordinated to the heteroaryl group) and the hole-injecting/transporting group (carbazolyl group) to be one. In particular, when used in a host or the like, the derivative of the invention can become a material which has excellent injecting/transporting properties of carriers.

Further, when $X_1$ to $X_8$ of $Z_1$ represented by the formula (2) is $CR_1$ and $R_1$ is not a hydrogen atom, $R_1$ as the substituent may preferably be an electron-attracting group such as a cyano group and a fluorine atom, an aryl group or a heteroaryl group. If $R_1$ is an electron-attracting group, $Z_1$ is allowed to be electron deficient, whereby a derivative having further excellent electron-injecting/transporting properties can be obtained. In addition, if $R_1$ is an aryl group or a heteroaryl group, a derivative can have excellent heat resistance.

In the specification, the "a to b carbon atoms" in the "substituted or unsubstituted XX group including a to b carbon atoms" means the number of carbon atoms if the XX group is unsubstituted, and does not include the number of carbon atoms of the substituent when the XX group is substituted. In addition, in the material for an organic EL device of the invention, a hydrogen atom includes an isotope differing in the number of neutrons, i.e. protium, deuterium and tritium.

In one embodiment of the invention, in the formula (1), it is preferred that $Z_2$ be carbazolyl, dibenzofuranyl, dibenzothiophenyl, fluorenyl, dibenzosilolyl, triphenylenyl, benzoimidazolyl, indolyl, benzofuranyl, benzothiophenyl, benzosilolyl, pyrimidinyl, triazinyl, quinolinyl, quinazolinyl, phenanthrolynyl, naphthyl, anthracenyl, phenanthryl, chrysenyl, pyrenyl, fluoranthenyl, phenoxazinyl, phenothiazinyl, phenoxathiinyl, a monovalent group of the following formula (3) ($R_4$, $R_5$ and $R_6$ are independently a substituted or unsubstituted alkyl group including 1 to 30 carbon atoms, a substituted or unsubstituted aryl group including 6 to 30 ring carbon atoms or a substituted or unsubstituted heteroaryl group including 5 to 30 ring atoms, or one of $R_4$, $R_5$ and $R_6$ is a single bond that is bonded to L), a monovalent group of the following formula (4) or a heteroaryl group obtained by substituting one or more of the carbon atoms forming a ring of these groups by a nitrogen atom (provided that the carbon atom at the ring-bonding site is not substituted by a nitrogen atom).

As the heteroaryl group obtained by substituting one or more of the atoms that form a ring (provided that the carbon atom at the ring-bonding site is not substituted by a nitrogen atom), azacarbazolyl, azadibenzofuranyl, azadibenzofuranyl, azadibenzothiophenyl, azafluorenyl, diazacarbazolyl, diazadibenzofuranyl, diazabenzothiophenyl, diazafluorenyl or the like can be given.

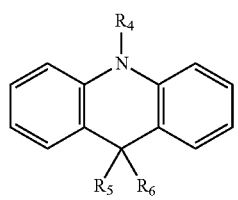

(3)

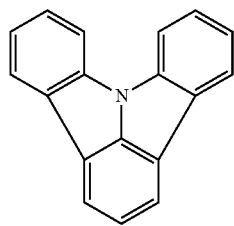

(4)

Examples of the alkyl group including 1 to 30 (preferably 1 to 6) carbon atoms in $R_4$, $R_5$ and $R_6$ are the same as those exemplified above referring to $A_1$ and $A_2$.

Examples of the aryl group including 6 to 30 (preferably 6 to 14) ring carbon atoms in $R_4$, $R_5$ and $R_6$ are the same as those exemplified referring to $Z_2$, L, $A_1$ and $A_2$.

Examples of the heteroaryl group including 5 to 30 (preferably 5 to 14) ring atoms in $R_4$, $R_5$ and $R_6$ are the same as those exemplified above referring to $Z_2$, L, $A_1$ and $A_2$.

In one embodiment of the invention, in the formula (1), $Z_2$ is preferably a group represented by the following formula (5):

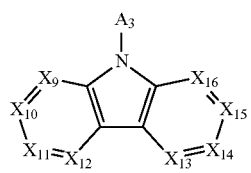

(5)

wherein in the formula (5), $X_9$ to $X_{16}$ are independently N (nitrogen atom) or $CR_7$ (C is a carbon atom);

$R_7$ is a single bond, a hydrogen atom or a substituent, and if plural $R_7$s are present, the plural $R_7$s may be the same or different;

$A_3$ is a single bond or a substituent; and one of $R_7$s or $A_3$ is a single bond that is bonded to L, provided that if L is a single bond, one of $R_7$s or $A_3$ is directly bonded to $Z_1$.

Further, it is more preferred that $A_3$ and L be a single bond and that a group represented by the formula (5) be bonded directly to $Z_1$.

Further, it is more preferred that $Z_2$ be 3-phenylcarbazolyl or 3,6-diphenylcarbazolyl. This enables the derivative to be one that is more stable to charges.

In one embodiment of the invention, it is preferred that $Z_2$ be a group represented by the following formula (6) or (7).

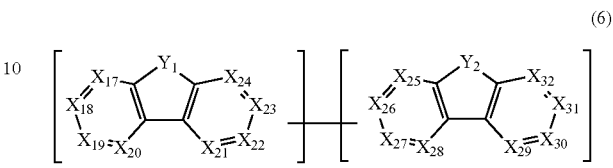

(6)

wherein in the formula (6), $X_{17}$ to $X_{32}$ are independently N (nitrogen atom) or $CR_8$ (C is a carbon atom), $R_8$ is a single bond, a hydrogen atom or a substituent, and if plural $R_8$s are present, the plural $R_8$s may be the same or different;

$Y_1$ and $Y_2$ are independently $NR_9$, O, S, $CR_{10}R_{11}$ or $SiR_{12}R_{13}$, and $R_9$, $R_{10}$, $R_{11}$, $R_{12}$ and $R_{13}$, that may be the same or different, are independently a single bond, a substituted or unsubstituted alkyl group including 1 to 30 carbon atoms, a substituted or unsubstituted aryl group including 6 to 30 ring carbon atoms or a substituted or unsubstituted heteroaryl group including 5 to 30 ring atoms;

one of $R_8$ to $R_{13}$ is a single bond and is bonded to L, provided that it is directly bonded to $Z_1$ if L is a single bond.

In addition to the single bond that is bonded to L, $R_8$ of $X_{17}$ to $X_{24}$ and any one of $R_9$ to $R_{13}$ of $Y_1$ and $R_8$ of $X_{25}$ to $X_{32}$ and any one of $R_9$ to $R_{13}$ of $Y_2$ are respectively a single bond, and the two single bonds are bonded with each other.

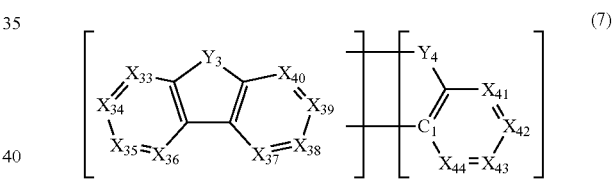

(7)

wherein in the formula (7), $X_{33}$ to $X_{44}$ are independently N (nitrogen atom) or $CR_{14}$ (C is a carbon atom), $R_{14}$ is a single bond, a hydrogen atom or a substituent, when plural $R_{14}$s are present, the plural $R_{14}$s may be the same or different;

$Y_3$ and $Y_4$ are independently $NR_{15}$, O, S, $CR_{16}R_{17}$ or $SiR_{18}R_{19}$; $R_{15}$, $R_{16}$, $R_{17}$, $R_{18}$ and $R_{19}$, that may be the same or different, are a single bond, a substituted or unsubstituted alkyl group including 1 to 30 carbon atoms, a substituted or unsubstituted aryl group including 6 to 30 ring carbon atoms or a substituted or unsubstituted heteroaryl group including 5 to 30 ring atoms;

$C_1$ is a carbon atom;

provided that, at least two of $X_{37}$ to $X_{40}$, being adjacent with each other, are both carbon atoms, and one of the two carbon atoms is bonded to $Y_4$ and the other is bonded to $C_1$; and one of $R_{14}$ to $R_{19}$ is a single bond and is bonded to L, provided that if L is a single bond, one of $R_{14}$ to $R_{19}$ is directly bonded to $Z_1$.

It is preferred that $Z_2$ be biscarbazolyl (when $Y_1$ and $Y_2$ are $NR_9$ and $X_{17}$ to $X_{32}$ are $CR_8$ in the formula (6)) or indolocarbazolyl (when $Y_3$ and $Y_4$ are $NR_{15}$ and $X_{33}$ to $X_{44}$ are $CR_{14}$ in the formula (7)). This enables the derivative to be one having excellent hole-injecting/transporting properties.

It is preferred that $Z_2$ be a group represented by the formula (7), and one of $Y_3$ and $Y_4$ be $CR_{16}R_{17}$ and the other be $NR_{15}$. This enables the derivative to be one having excellent hole-injecting/transporting properties.

Examples of the alkyl group including 1 to 30 (preferably 1 to 6) carbon atoms in $R_{15}$, $R_{16}$, $R_{17}$, $R_{18}$ and $R_{19}$ are the same as those exemplified above referring to $A_1$ and $A_2$.

Examples of the aryl group including 6 to 30 (preferably 6 to 14) ring carbon atoms in $R_{15}$, $R_{16}$, $R_{17}$, $R_{18}$ and $R_{19}$ are the same as those exemplified above referring to $Z_2$, L, $A_1$ and $A_2$.

Examples of the heteroaryl group including 5 to 30 (preferably 5 to 14) ring atoms are the same as those exemplified above referring to $Z_2$, L, $A_1$ and $A_2$.

Examples of the substituent in $R_7$, $R_8$ and $R_{14}$ are the same as those exemplified above referring to $R_1$.

In one embodiment of the invention, it is preferred that $A_1$ and $A_2$ in the formula (2) be independently be a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted alkoxy group including 1 to 30 carbon atoms, a substituted or unsubstituted aryloxy group including 6 to 30 ring carbon atoms, a substituted or unsubstituted alkylamino group including 1 to 30 carbon atoms, or a substituted or unsubstituted arylamino group including 6 to 30 ring carbon atoms.

it is more preferred that $A_1$ and $A_2$ be independently a mesityl group, an aryl group having a substituent in one or two atoms that are adjacent to an atom that is bonded to B (boron atom) or a heteroaryl group having a substituent in one or two atoms that are adjacent to an atom that is bonded to B (boron atom). Due to the presence of these groups, a derivative having excellent heat resistance can be obtained.

In one embodiment of the invention. $A_1$ in the formula (2) be a substituted or unsubstituted aryl group including 6 to 30 ring carbon atoms, a substituted or unsubstituted heteroaryl group including 5 to 30 ring atoms, an unsubstituted alkyl group including 1 to 30 carbon atoms, a substituted or unsubstituted alkoxy group including 1 to 30 carbon atoms, a substituted or unsubstituted aryloxy group including 6 to 30 ring carbon atoms, a substituted or unsubstituted alkylamino group including 1 to 30 carbon atoms, or a substituted or unsubstituted arylamino group including 6 to 30 ring carbon atoms, or a halogen atom.

By appropriately selecting groups to be combined, the heteroarene derivative of the invention that comprises a nitrogen-boron coordinate bond according to the invention can be a derivative that is preferable as a material for various layers of an organic EL device.

Specifically, by combining the hetroarene derivative of the invention that comprises a nitrogen-boron coordinate bond with a hole-injecting/transporting group such as carbazole, carrier balance can be controlled, and hence, the derivative can be a derivative suitable for use as a host material or a layer adjacent to an emitting layer.

Further, by combining the heteroarene derivative of the invention that comprises a nitrogen-boron coordinate bond with an electron-injecting/transporting group such as benzoimidazole or dibenzofuran, the derivative can be a derivative suitable for use as an electron-transporting host material or a material for a layer nearer to the cathode.

For example, by combining the heteroarene derivative of the invention that comprises a nitrogen-boron coordinate bond with a fused ring such as triphenylene, heat resistance of a material can be improved. In addition, fine carrier balance control can become possible.

The heteroarene derivative of the invention can be produced by a technique described in the following synthesis examples. The production method is not particularly restricted, and the heteroarene derivative can be produced by a known method. For example, it can be produced by a method stated in Journal of Organic Chemistry, 2010, Vol. 75, pp. 8709-8712 and Angewabdte Chemie International Edition, 2011, Vol. 50, pp. 11724 to 11728.

Specific examples of the heteroarene derivative according to the invention that comprises a nitrogen-boron coordinate bond are shown below, though not limited thereto.

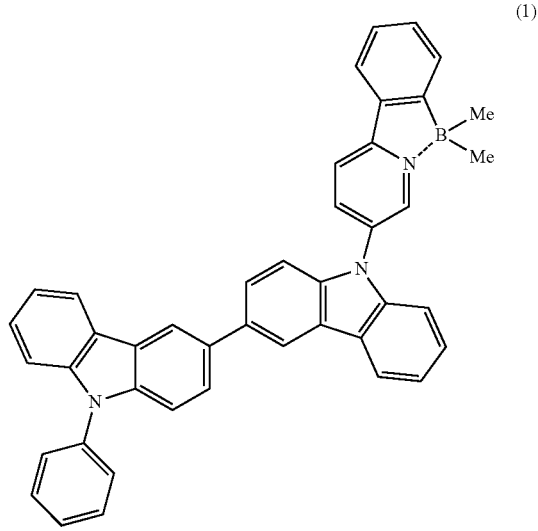

(1)

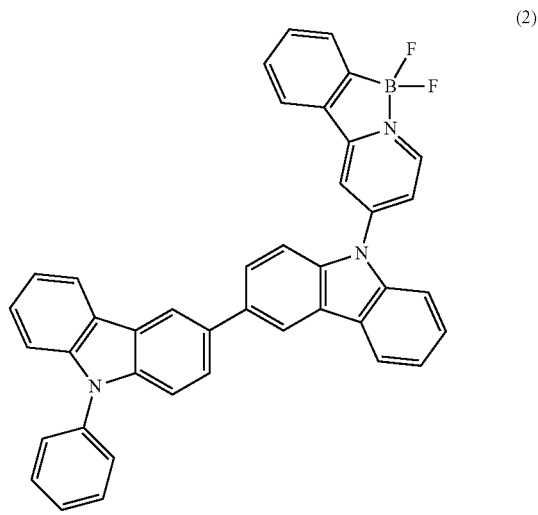

(2)

-continued
(3)
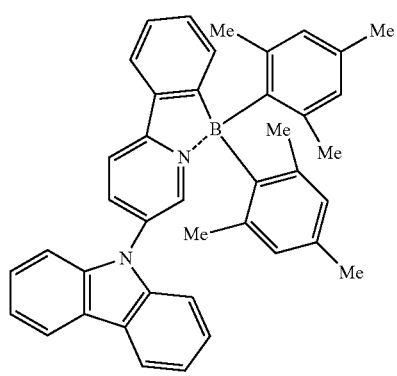
(4)
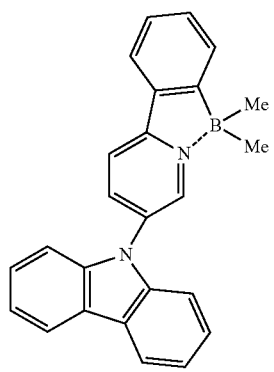
(5)
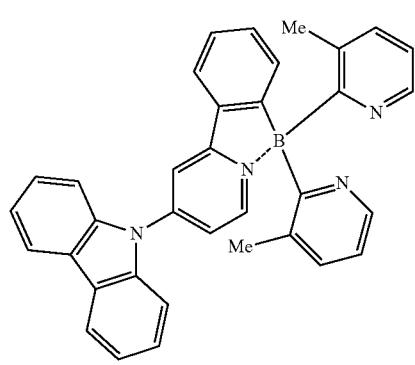
(6)
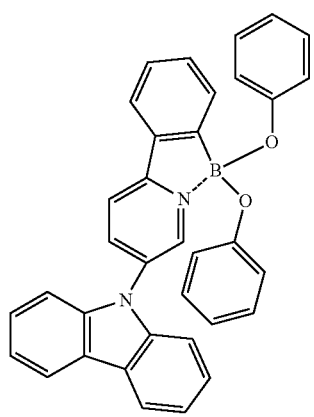
-continued
(7)
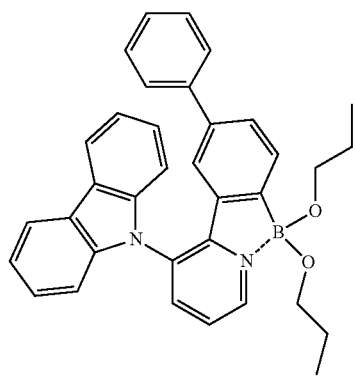
(8)
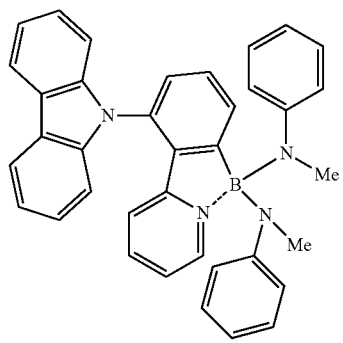
(9)
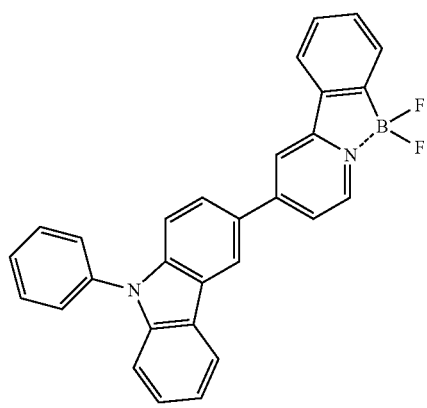
(10)

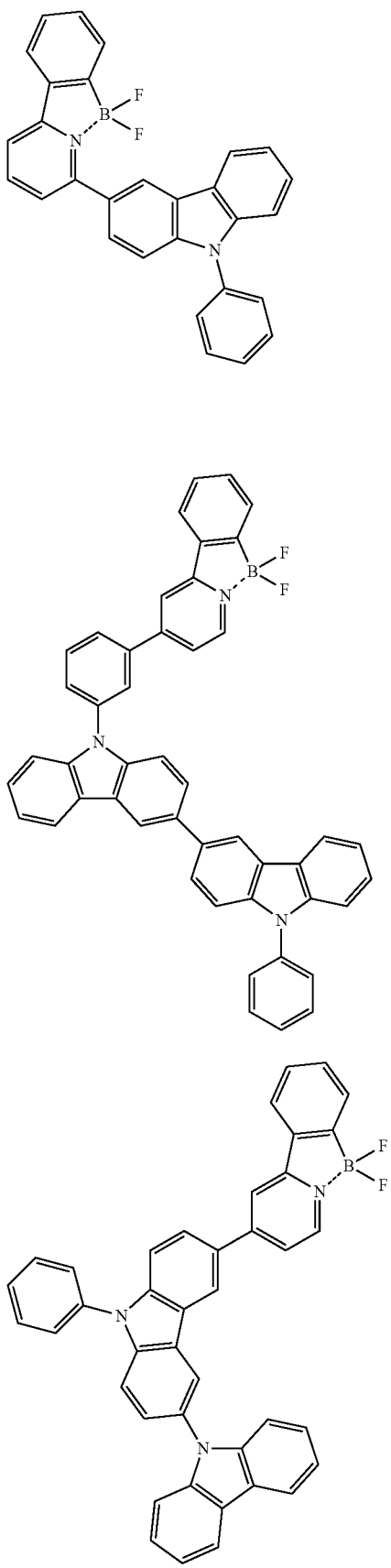
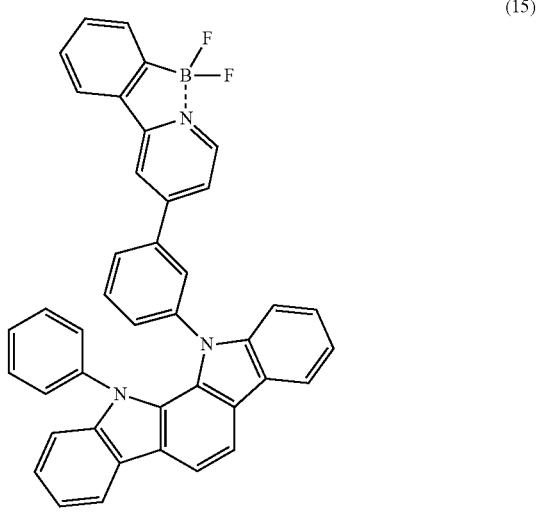
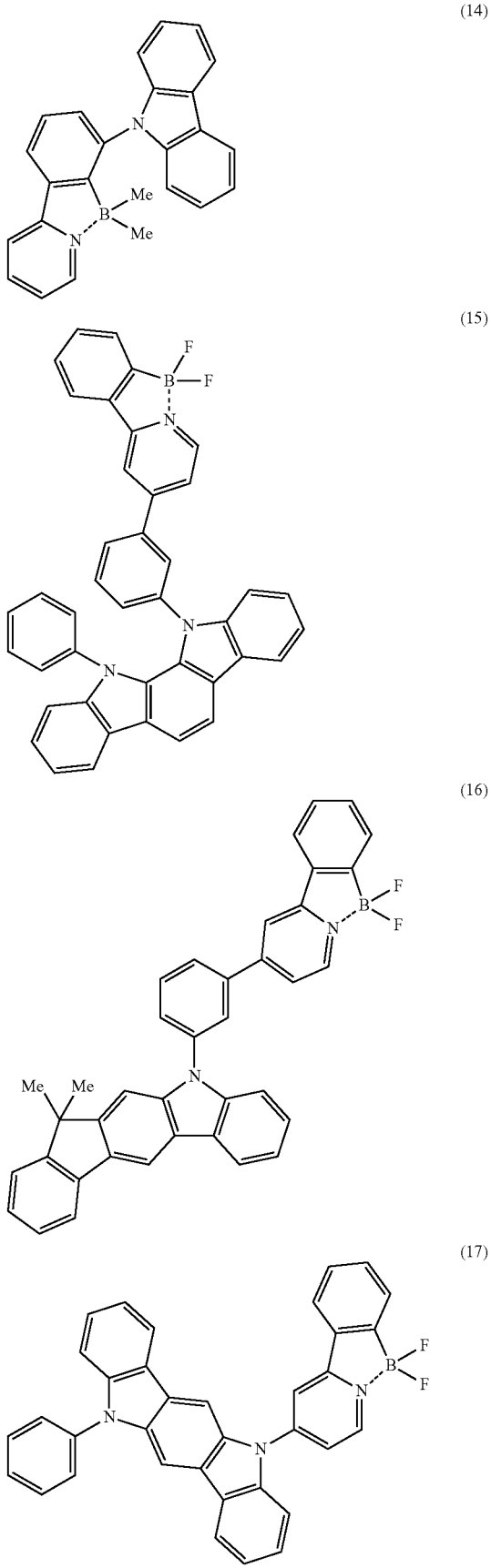
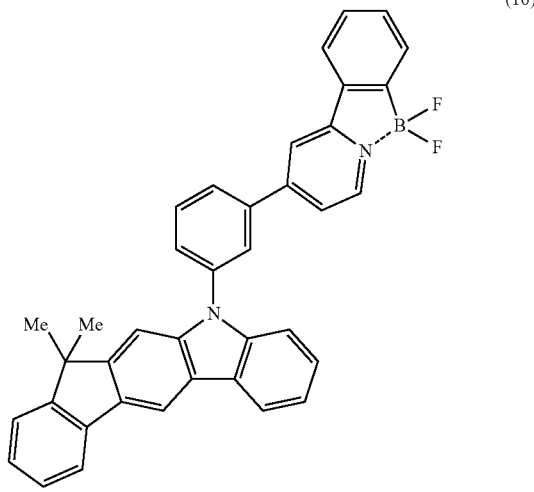
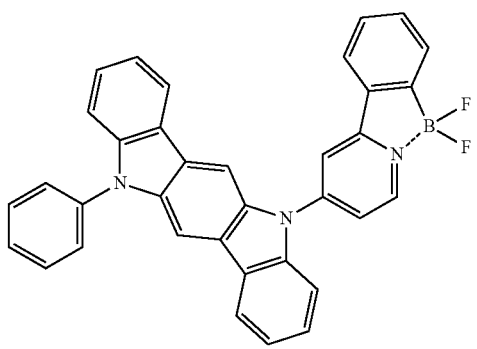

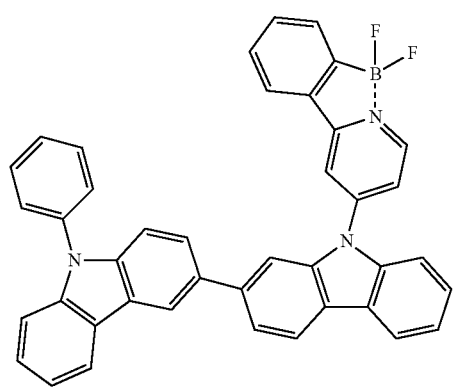
(18)
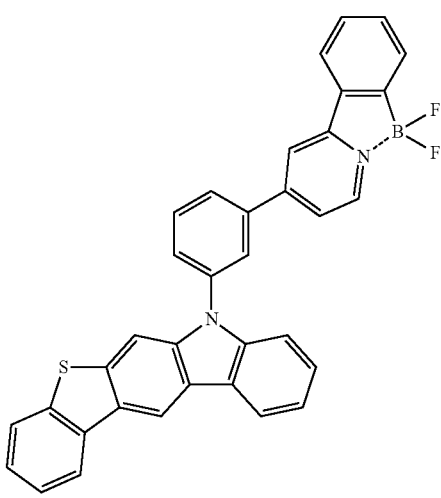
(21)
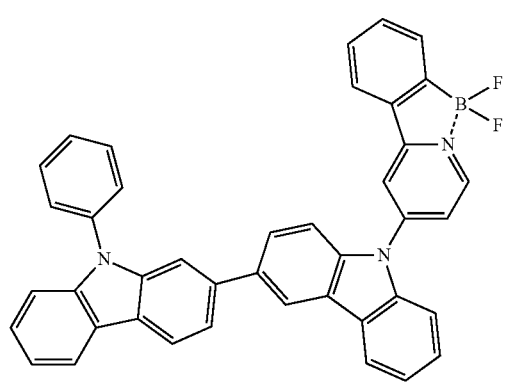
(19)
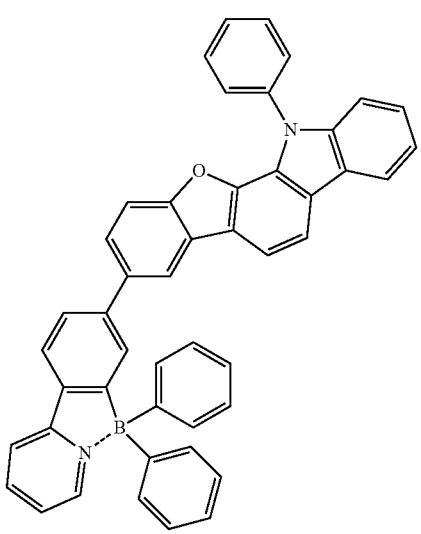
(22)
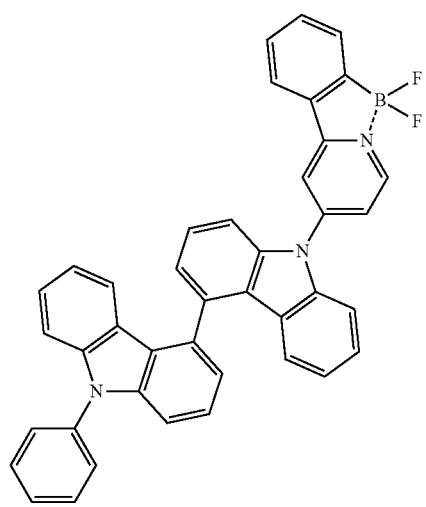
(20)
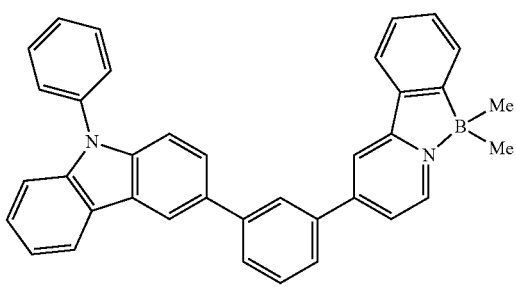
(23)

(24)
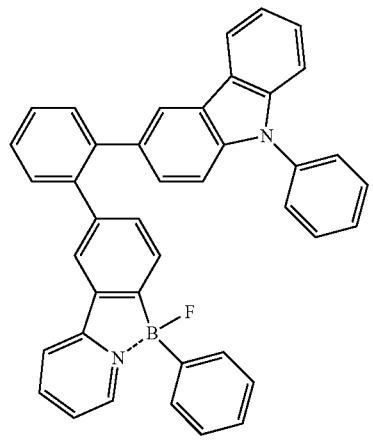
(25)
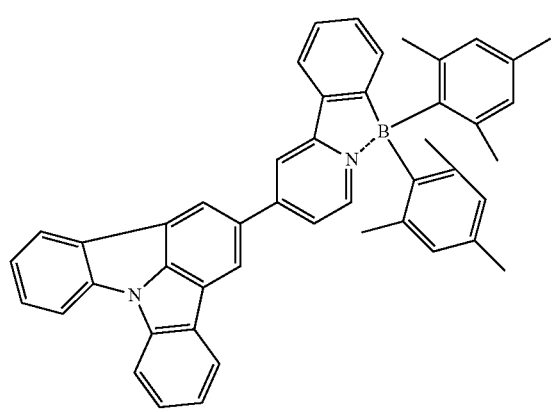
(26)
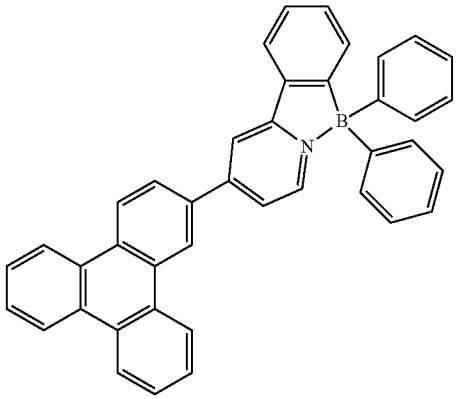
(27)
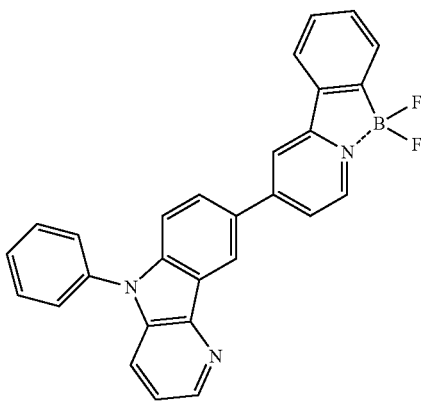
(28)
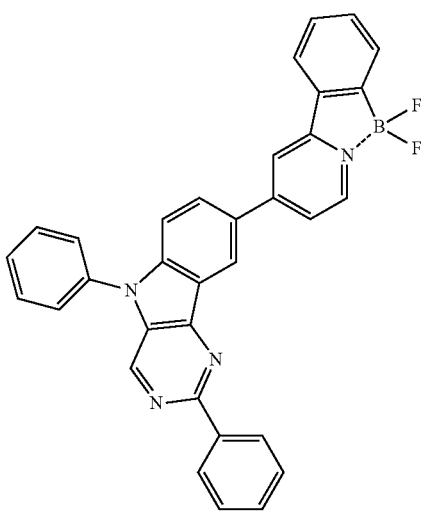
(29)
(30)
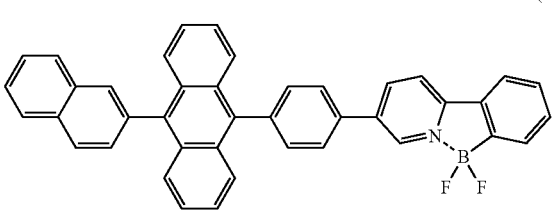

(31)
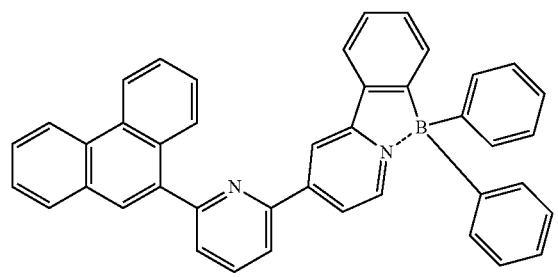
(32)
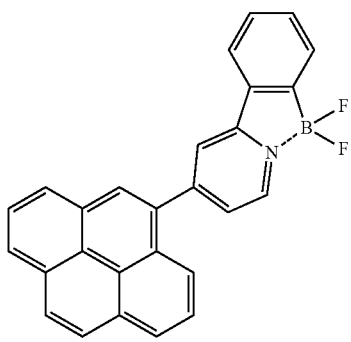
(33)
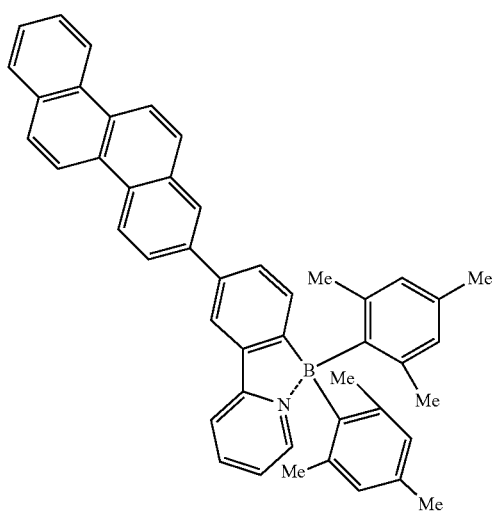
(34)
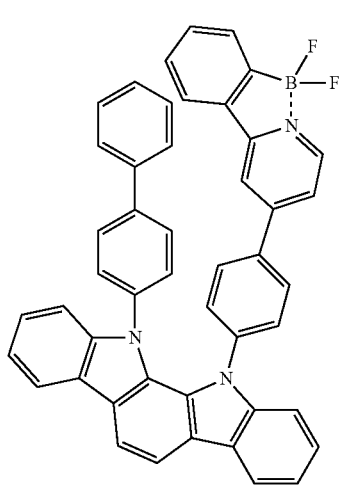
(35)
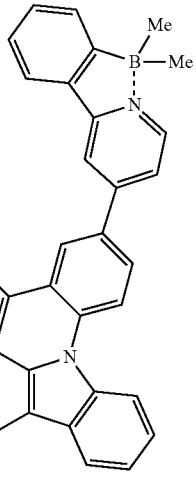
(36)
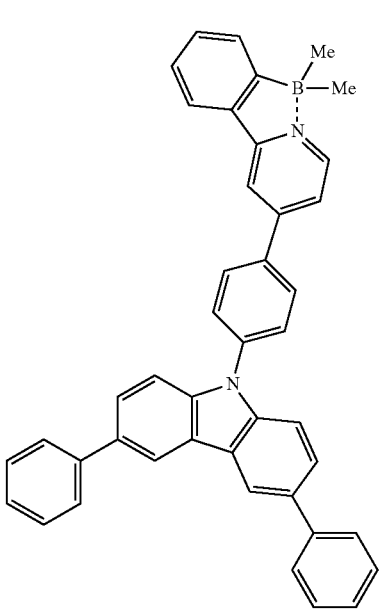
(37)
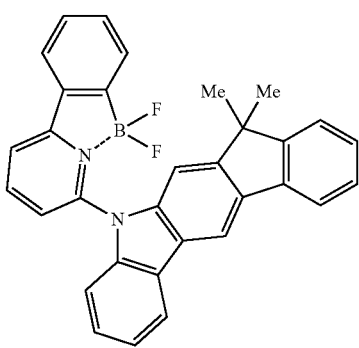

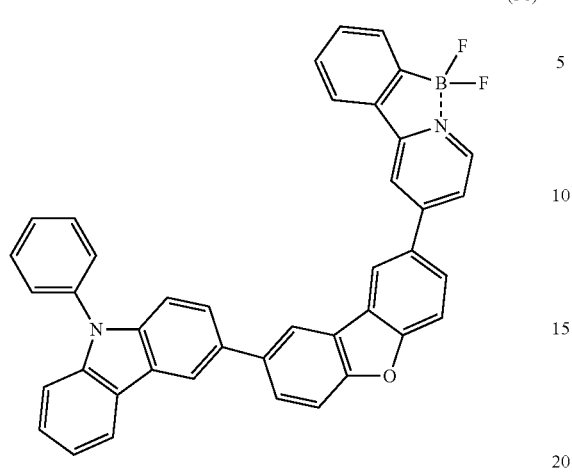
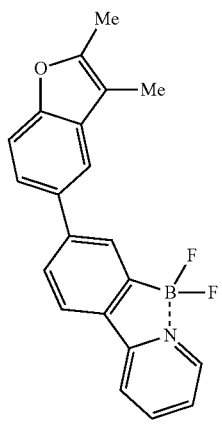
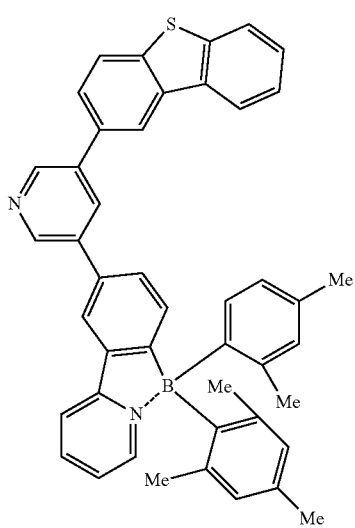

(44) 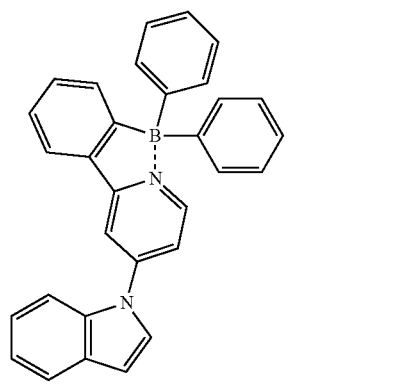
(45) 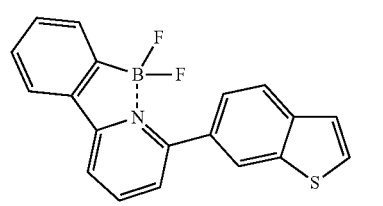
(46) 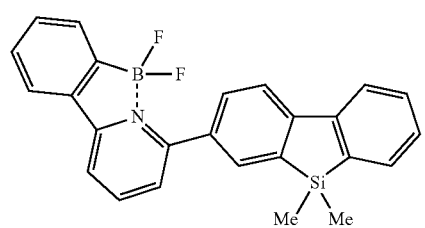
(47) 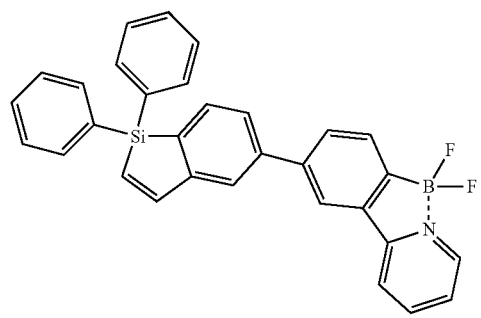
(48) 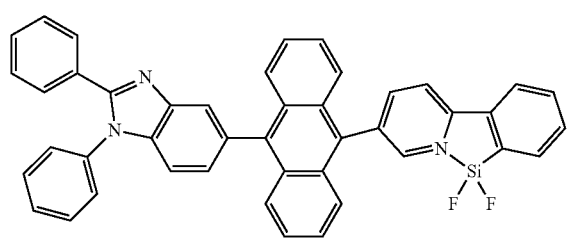
(49) 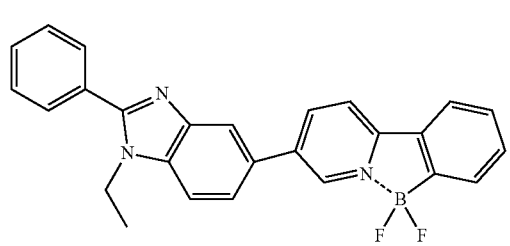
(50) 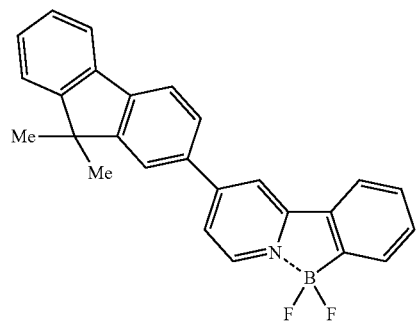
(51) 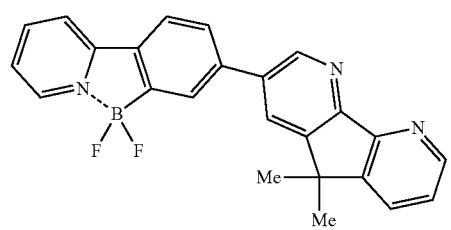
(52) 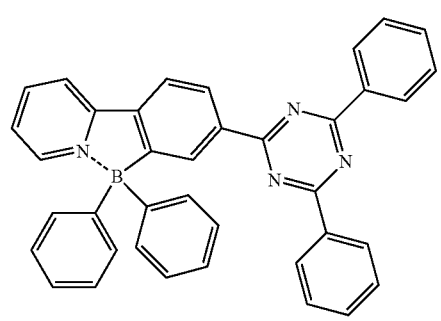
(53) 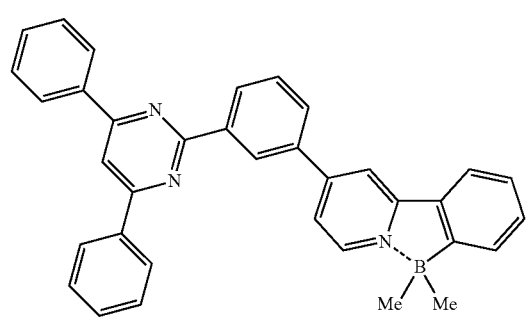
(54) 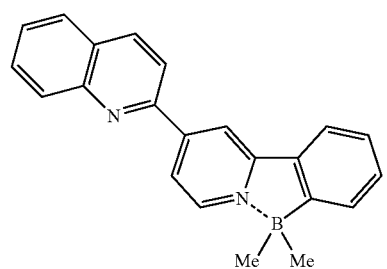

(55) 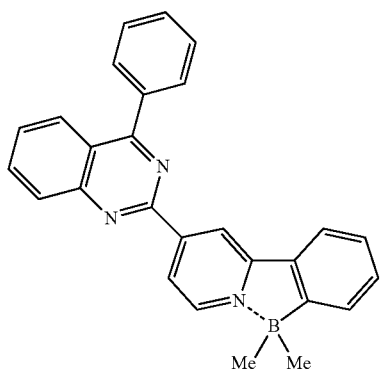
(56) 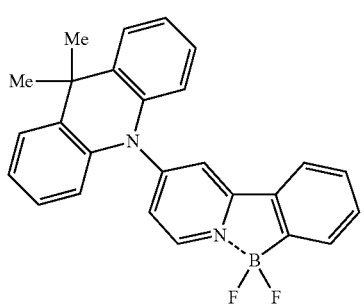
(57) 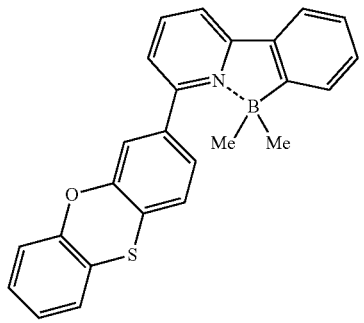
(58) 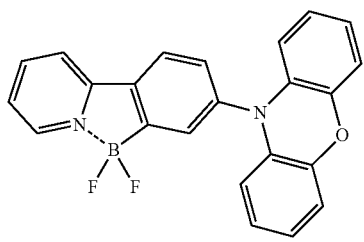
(59) 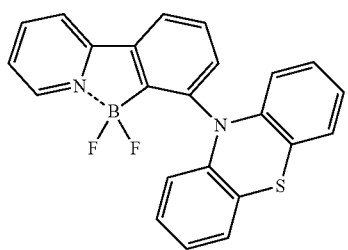
(60) 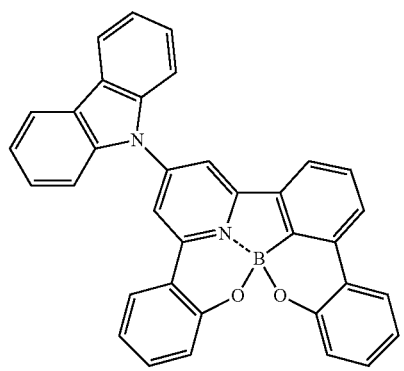
(61) 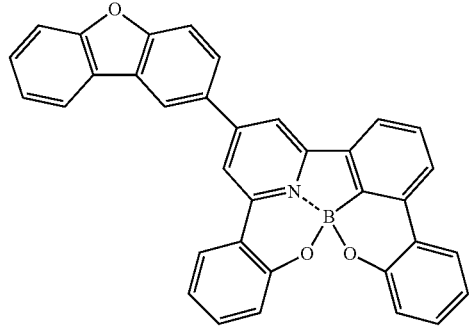
(62) 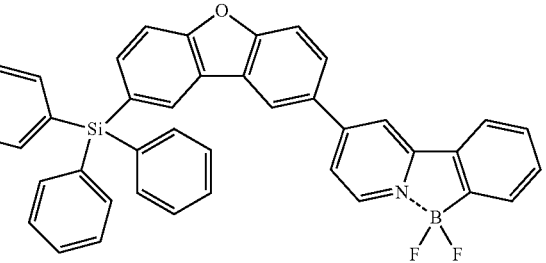
(63) 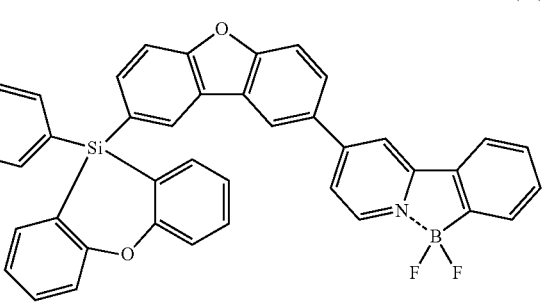

-continued
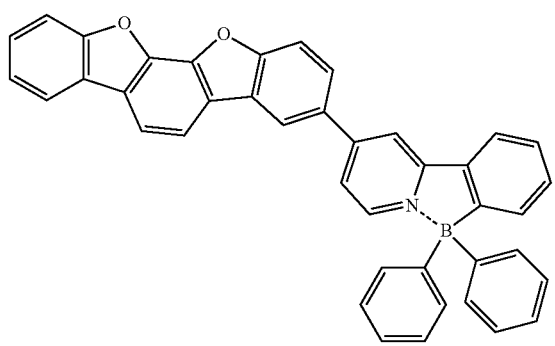
(64)
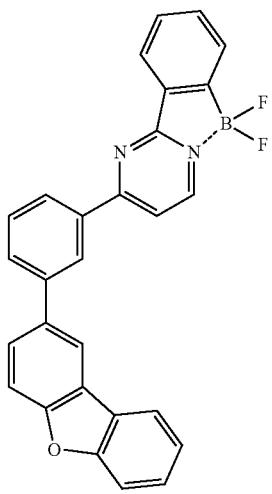
(65)
(66)
(67)
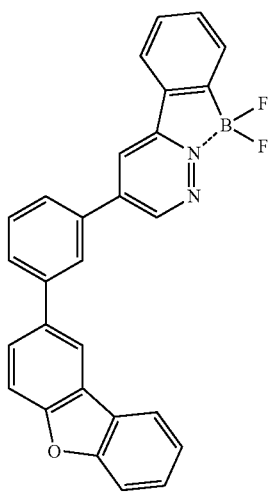
(68)
(69)
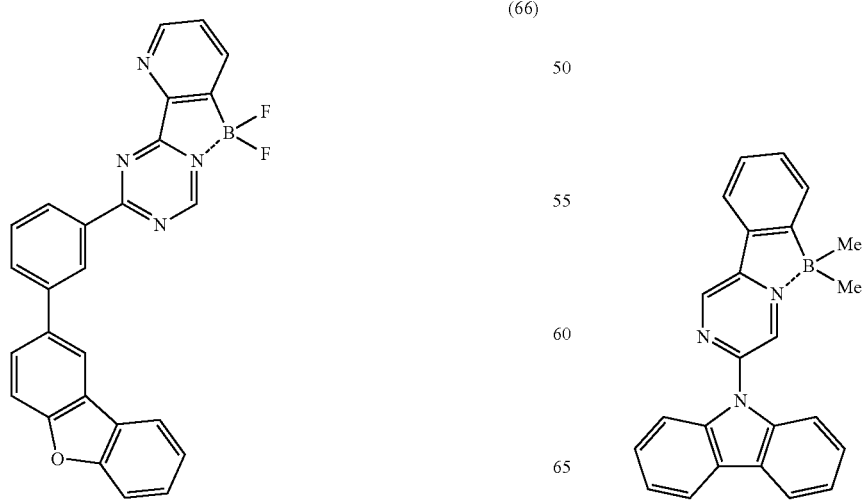

-continued
(70)
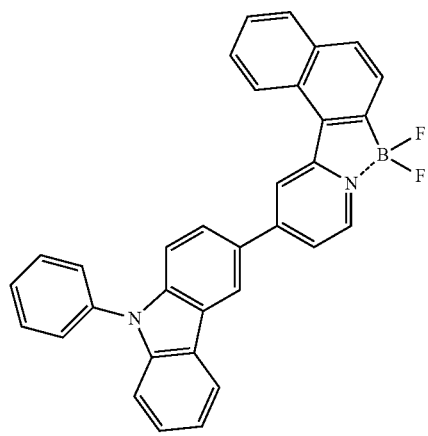
(71)
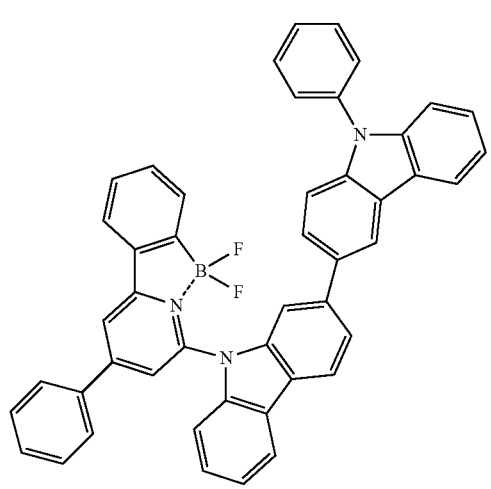
(72)
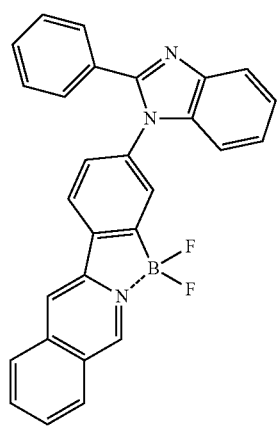
-continued
(73)
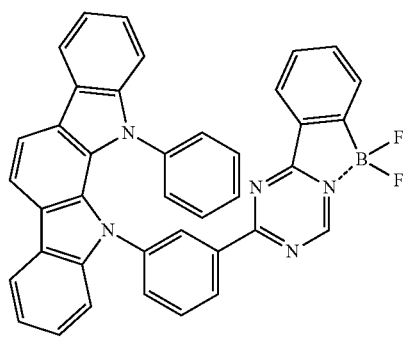
(74)
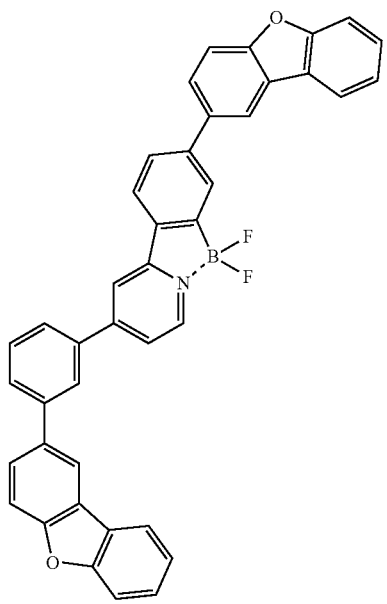
(75)
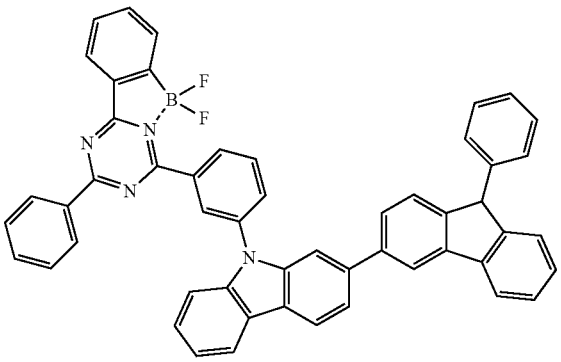

-continued
(76)
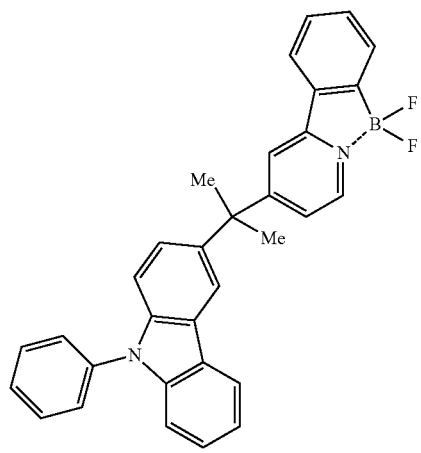
(77)
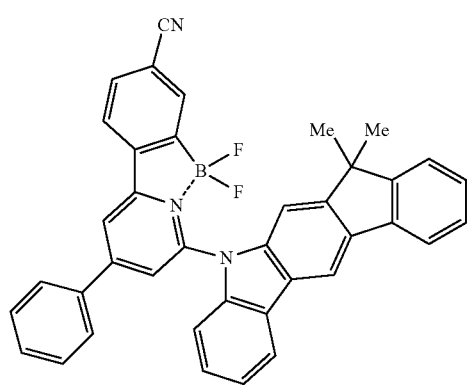
(78)
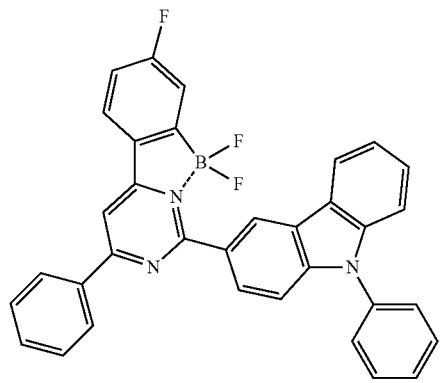
(79)
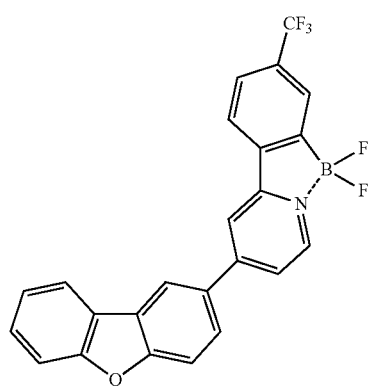
-continued
(80)
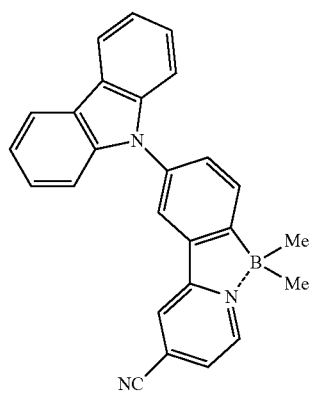
(81)
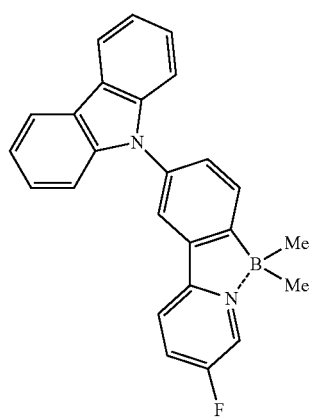
(82)
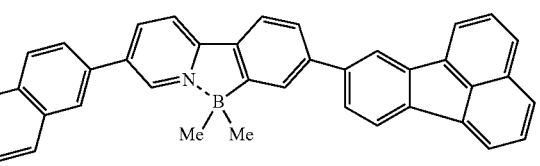
(83)
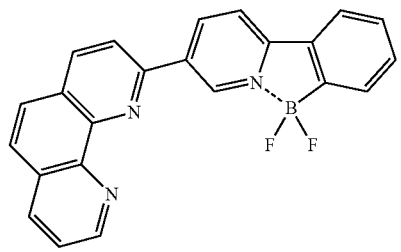
(84)
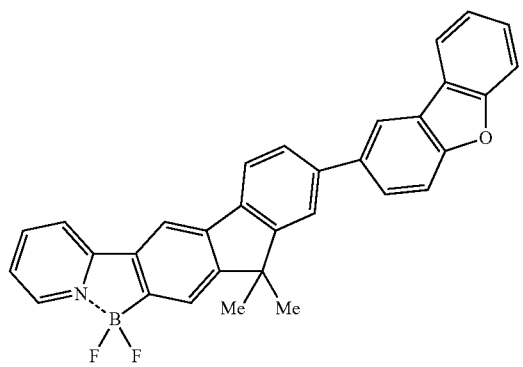

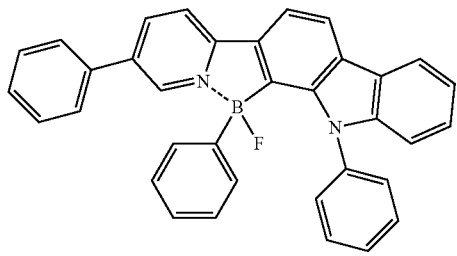
(85)
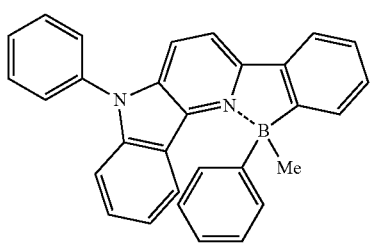
(86)
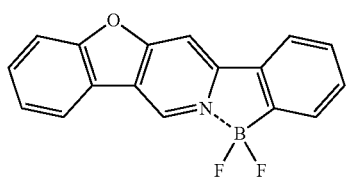
(87)
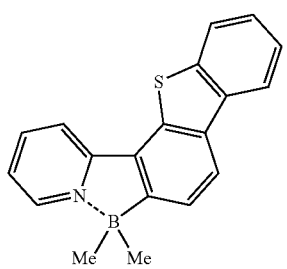
(88)
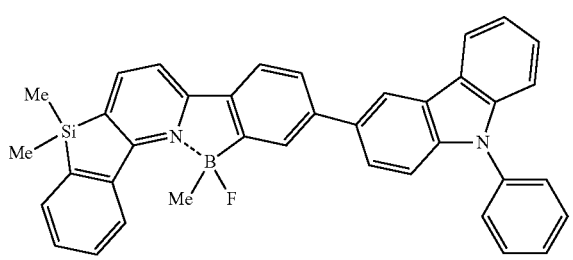
(89)
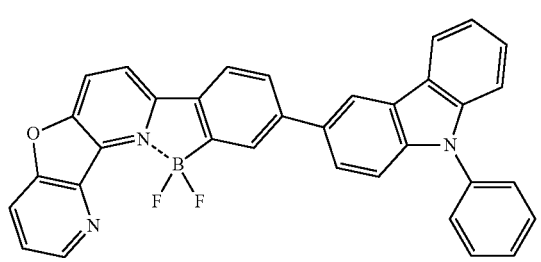
(90)
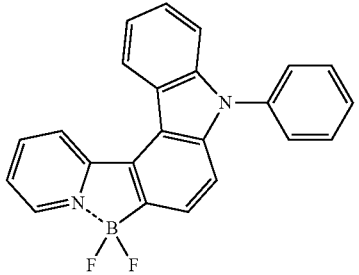
(91)
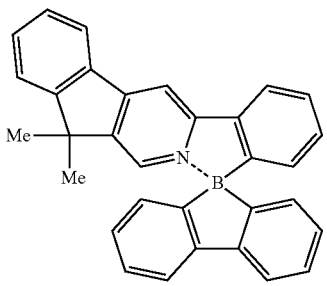
(92)
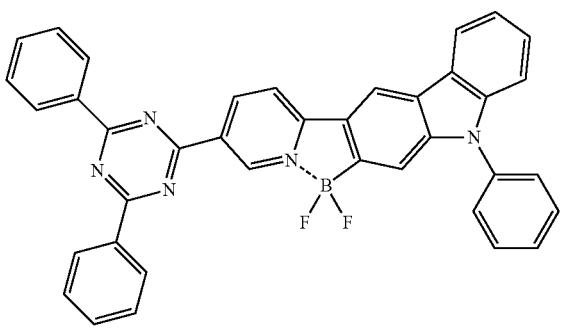
(93)
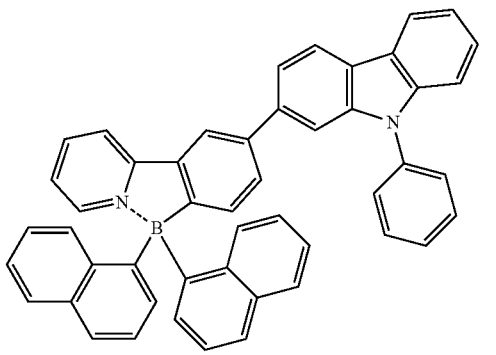
(94)
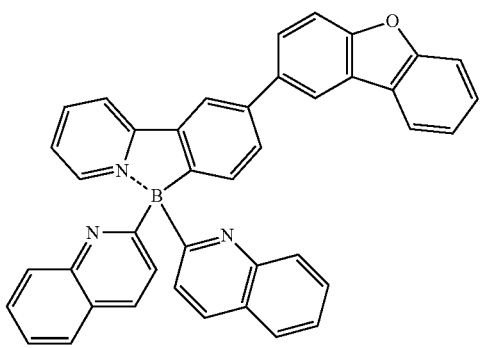
(95)

(96) 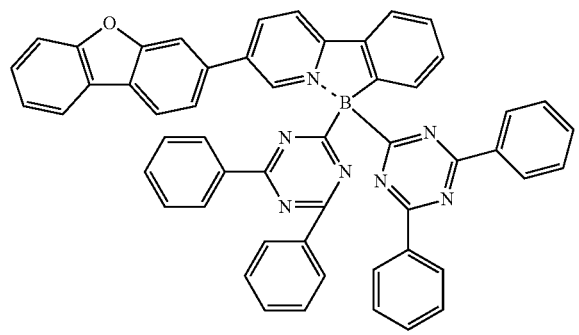

(97) 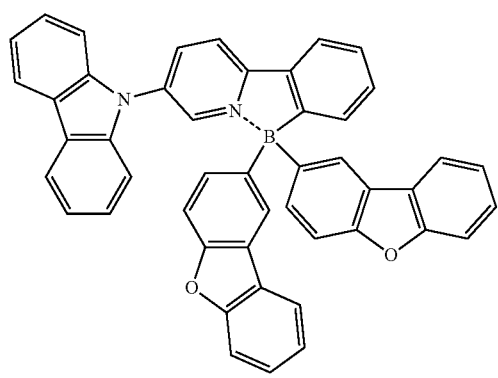

(98) 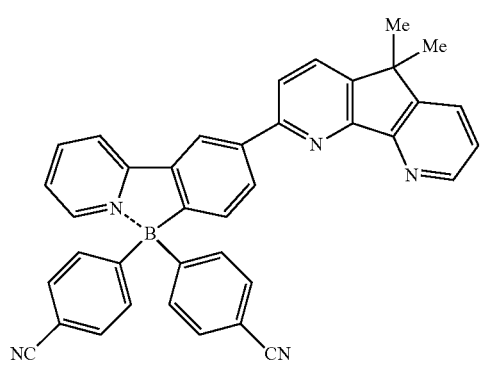

(99) 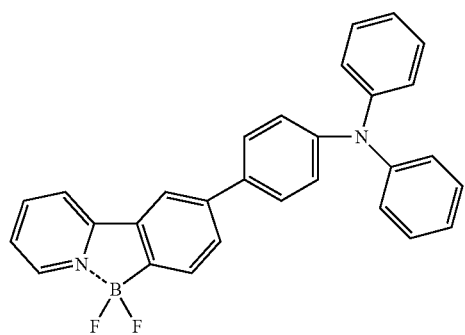

(100) 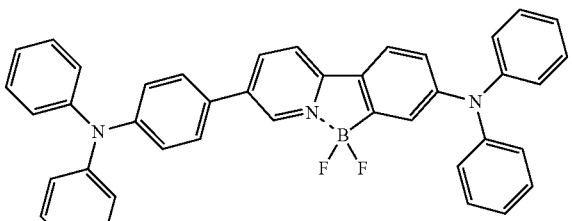

(101) 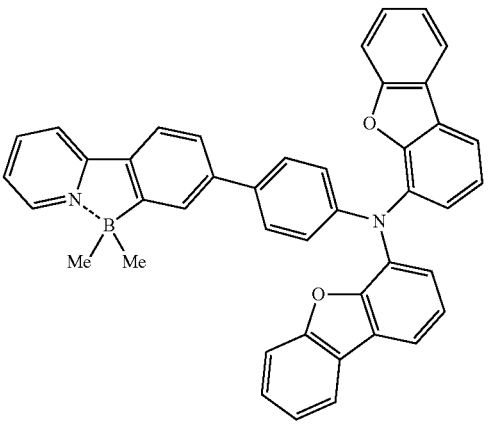

The material for an organic EL device of the invention comprises the heteroarene derivative of the invention that comprises a nitrogen-boron coordinate bond. The material for an organic EL device of the invention may comprise other materials which are known in this technical field.

The organic EL device of the invention comprises one or more organic thin film layers including an emitting layer between a cathode and an anode, and at least one layer of the organic thin film layers comprises the above-mentioned material for an organic EL device of the invention.

One embodiment of the organic EL device of the invention will be explained.

The organic EL device of the invention has a configuration in which, on a substrate, an anode, a hole-transporting region, an emitting layer, an electron-transporting region and a cathode are stacked in this sequence. The hole-transporting region means a hole-transporting layer and/or a hole-injecting layer or the like. Similarly, the electron-transporting region means an electron-transporting layer and/or an electron-injecting layer or the like. Although these layers may not be formed, it is preferred that one or more of these layers be formed. In the device of this embodiment, the organic thin film layers are organic thin film layers provided in the hole-transporting region or organic thin film layers provided in the emitting layer and the electron-transporting region. Among these organic thin film layers, at least one layer comprises the material for an organic EL device of the invention.

The content of this material in the organic thin film layers comprising the material for an organic EL device according to the invention is preferably 1 to 100 mass %.

Examples of the organic thin film layer comprising the material for an organic EL device of the invention include, though not limited thereto, a hole-transporting layer, an emitting layer, an electron-transporting layer, a hole-injecting layer, an electron-injecting layer, a space layer, a barrier

EXAMPLES

The invention will be explained in more detail with reference to the Examples, which should not be construed as limiting the scope of the invention.

Synthesis Example 1

Synthesis of Compound (1)

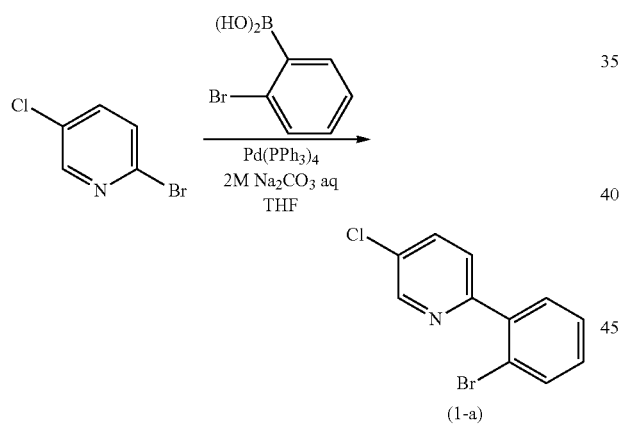

In a three-neck flask, 9.62 g (50.0 mmol) of 2-bromo-5-chloropyridine, 12.0 g (60.0 mmol) of 2-bromophenylboronic acid, 1.44 g (1.25 mmol) of tetrakis(triphenylphosphine)palladium (0), 70 mL of tetrahydrofuran and 70 mL of a 2M aqueous sodium carbonate solution were placed. The resulting mixture was stirred at 75° C. for 12 hours in a nitrogen atmosphere.

After completion of the reaction, 50 ml of water was added to the reaction solution. The resulting mixture was transferred to a separating funnel, and extracted with ethyl acetate several times. The extracted product was dried with anhydrous magnesium sulfate, filtered and concentrated. The concentrate was purified by silica gel chromatography (hexane:dichloromethane=1:1), whereby compound (1-a) was obtained as white solids.

The yield was 9.00 g (67%).

(2) Synthesis of Compound (1-b)

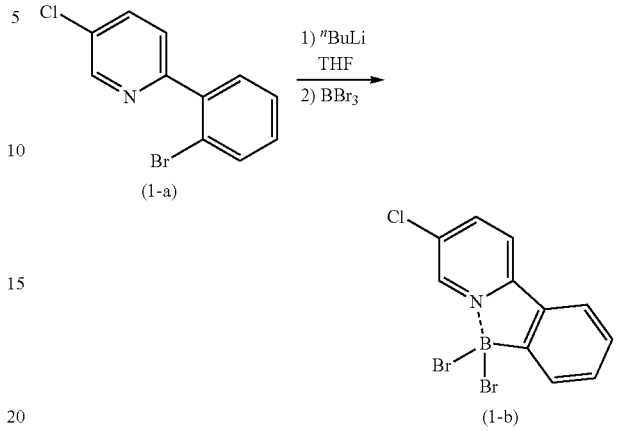

In a three-neck flask, 7.73 g (28.8 mmol) of compound (1-a) was placed. In a nitrogen atmosphere, 40 mL of tetrahydrofuran was added, and the reaction solution was cooled to −78° C. To the thus cooled reaction solution, 18.3 mL (1.57M, 28.8 mmol in hexane) of n-butyllithium was added dropwise. After stirring at −78° C. for 20 minutes, 28.8 mL of boron tribromide (1.00M, 28.8 mmol in dichloromethane) was added, followed by stirring for 14 hours at room temperature.

After completion of the reaction, in an ice bath, an aqueous potassium carbonate solution was added. The resulting mixture was transferred to a separating funnel, and extracted with dichloromethane several times. The resulting organic phase was dried with anhydrous magnesium sulfate, filtered and concentrated. The concentrate was purified by suspending in and washing with hexane, whereby compound (1-b) was obtained as white solids.

The yield was 7.06 g (68%).

(3) Synthesis of Compound (1-c)

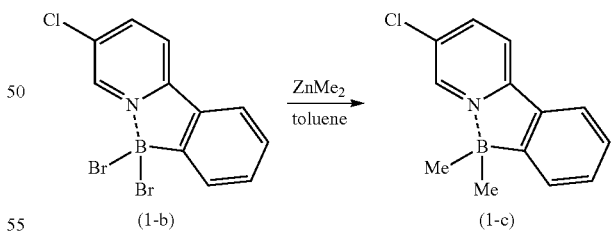

In a three-neck flask, 7.10 g (19.7 mmol) of compound (1-b) and 190 mL of toluene were placed. In a nitrogen atmosphere, 10.8 mL (21.7 mmol) of a 2M toluene solution of dimethyl zinc was added, and the resulting mixture was stirred at 70° C. For 10 hours.

After completion of the reaction, in an ice bath, water was added. The resulting solution was transferred to a separating funnel, and extracted with ethyl acetate several times. The resulting organic phase was dried with anhydrous magnesium sulfate, filtered and concentrated. The concentrate was purified by silica gel chromatography (hexane:dichloromethane=2:1), whereby compound (1-c) was obtained as white solids.

The yield was 3.88 g (95%).

(4) Synthesis of Compound (1)

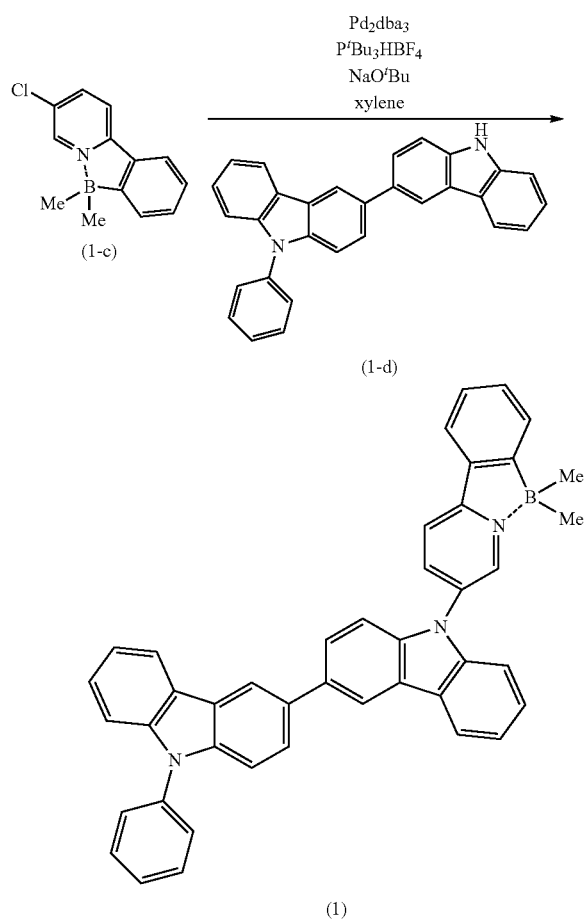

In a three-neck flask, 2.26 g (9.80 mmol) of compound (1-c), 2.86 g (7.00 mmol) of compound (1-d), 0.128 g (0.140 mmol) of tris(dibenzylideneacetone)dipalladium(0), 0.163 g (0.560 mmol) of tri-tert-butylphosphonium tetraphenylborate, 1.35 g (14.0 mmol) of sodium tert-butoxide and 35 mL of xylene were placed. The resulting mixture was refluxed with heating for 16 hours in a nitrogen atmosphere.

After completion of the reaction, precipitated solids were collected by filtration, and purified by silica gel chromatography (toluene), whereby compound (1) was obtained as pale yellow solids.

The yield was 2.40 g (57%).

Compound (1-d) can be synthesized by a method stated in the WO2012/121561 or by other methods.

The peaks of the $^1$HNMR (400 MHz) of the compound (1) were as follows.

$^1$HNMR (CDCl$_3$): δ0.16 (S, 6H), 7.32-7.53 (m, 11H), 7.61-7.64 (m, 4H), 7.70 (d, J=7.6 Hz, 1H), 7.76 (dd, J=8.6, 1.6 Hz, 1H), 7.85 (dd, J=8.6, 1.6 Hz, 1H), 7.93 (d, J=8.0 Hz, 1H), 8.18 (d, J=8.8 Hz, 1H), 8.24-8.28 (m, 3H), 8.47 (dd, J=4.6, 1.6 Hz, 2H), 8.79 (d, J=1.6 Hz, 1H).

The triplet energy of the compound (1) synthesized in the above-mentioned Synthesis Example is shown in Table 1. The triplet energy was measured by means of F-4500 (manufactured by Hitachi Ltd.). The conversion formula of the triplet energy is as follows.

Conversion formula: Triplet energy (eV)=1239.85/$\lambda_{ph}$

In the formula, the "$\lambda_{ph}$ (unit: nm)" means, when the phosphorescent intensity and the wavelength are taken at the vertical axis and the horizontal axis respectively to express a phosphorescent spectrum and a tangential line is drawn against the rise on the shorter wavelength side of the phosphorescent spectrum, a wavelength value of the intersection of the tangential line and the horizontal axis.

Compound (1) was dissolved in a solvent (the compound (1): 10 μmol/l, EPA (diethyl ether:isopentane:ethanol=5:5:2 (volume ratio), each solvent was a spectroscopy grade solvent), thereby to obtain a sample for measuring phosphorescence emission. The sample for measuring the phosphorescence emission that had been placed in a quarts cell was cooled to 77 (K). The sample was irradiated with excited light, and the phosphorescent intensity was measured while changing the wavelength. In the phosphorescent spectrum, the vertical axis was taken as the phosphorescent intensity and the horizontal axis was taken as the wavelength.

A tangential line was drawn against the rise on the shorter wavelength side of the phosphorescent spectrum, and the wavelength value $\lambda_{ph}$ (nm) of the intersection of the tangential line and the horizontal axis was obtained.

The tangential line against the rise on the shorter wavelength side of the phosphorescent spectrum was drawn as follows. Viewing the tangential line at each point on the spectrum curve from the shorter wavelength side of the phosphorescent spectrum to the maximum value on the shortest wavelength side, the slope of each of these tangential lines increases with the rise on the curve (i.e. as the vertical axis increases). The tangential line drawn at a point where the value of the slope becomes maximum was taken as the tangential line drawn against the rise on the shorter wavelength side of the phosphorescent spectrum.

The maximum point having a peak intensity that is 10% or less of the maximum peak intensity of the spectrum is not included in the maximum value of the above-mentioned maximum value of the shortest wavelength side, and a tangential line drawn at a point (a point nearest to the maximum value in the shortest wavelength range) where the value of the slope becomes the maximum is taken as a tangential line against the rise of the shortest wavelength side of the phosphorescent spectrum.

TABLE 1

| Compound | Triplet energy (eV) |
| --- | --- |
| Compound (1) | 2.75 |

As shown in Table 1, compound (1) which is the heteroarene compound of the invention has a triplet energy that is applicable as the material for an organic EL device.

INDUSTRIAL APPLICABILITY

The heteroarene derivative according to the invention that comprises a nitrogen-boron coordinate bond can be preferably used as the material for an organic electroluminescence device.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification and the Japanese application specification claiming priority under the Paris Convention are incorporated herein by reference in its entirety.

The invention claimed is:

1. A heteroarene derivative comprising a nitrogen-boron coordinate bond, represented by the following formula (1):

$$Z_1\text{-}L\text{-}Z_2 \quad (1)$$

wherein in the formula (1), $Z_1$ is a group represented by the following formula (2);

$Z_2$ is a group represented by the following formula (6) or (7);

L is a substituted or unsubstituted arylene including 6 to 30 ring carbon atoms, a substituted or unsubstituted heteroarylene including 5 to 30 ring atoms, —O—, —S—, —(CR$_2$R$_3$)$_n$— (wherein n is an integer of 1 to 8, and R$_2$ and R$_3$ are independently a substituted or unsubstituted alkyl group including 1 to 30 carbon atoms, a substituted or unsubstituted aryl group including 6 to 30 ring carbon atoms or a substituted or unsubstituted heteroaryl group including 5 to 30 ring atoms) or a single bond;

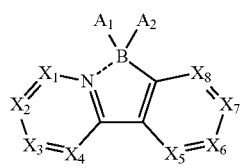

(2)

wherein in the formula (2), $X_1$ to $X_8$ are independently N (nitrogen atom) or CR$_1$ (C is a carbon atom);

R$_1$ is a single bond, a hydrogen atom or a substituent, and if plural R$_1$s are present, the plural R$_1$s may be the same or different;

one of $X_1$ to $X_8$ is CR$_1$ in which R$_1$ is a single bond and R$_1$ is bonded to L, provided that, if L is a single bond, R$_1$ is bonded directly to $Z_2$;

and if the remainder of $X_1$ to $X_8$ is independently CR$_1$, R$_1$ is not the same as -L-$Z_2$;

$A_1$ and $A_2$ are independently a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted alkoxy group including 1 to 30 carbon atoms, a substituted or unsubstituted aryloxy group including 6 to 30 ring carbon atoms, a substituted or unsubstituted alkylamino group including 1 to 30 carbon atoms, a substituted or unsubstituted arylamino group including 6 to 30 ring carbon atoms or a halogen atom;

a broken line between B and N is a coordinate bond;

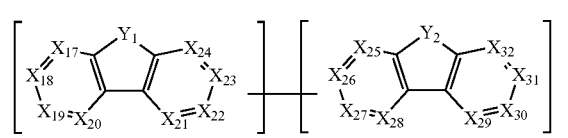

(6)

wherein in the formula (6), $X_{17}$ to $X_{32}$ are independently N (nitrogen atom) or CR$_8$ (C is a carbon atom);

R$_8$ is a single bond, a hydrogen atom or a substituent; and if plural R$_8$s are present, the plural R$_8$s may be the same or different;

$Y_1$ and $Y_2$ are independently NR$_9$, O, S, CR$_{10}$R$_{11}$ or SiR$_{12}$R$_{13}$, and R$_9$, R$_{10}$, R$_{11}$, R$_{12}$ and R$_{13}$, that may be the same or different, are a single bond, a substituted or unsubstituted alkyl group including 1 to 30 carbon atoms, a substituted or unsubstituted aryl group including 6 to 30 ring carbon atoms or a substituted or unsubstituted heteroaryl group including 5 to 30 ring atoms;

one of R$_8$ to R$_{13}$ is a single bond and is bonded to L, provided that if L is a single bond, one of R$_8$ to R$_{13}$ is directly bonded to $Z_1$;

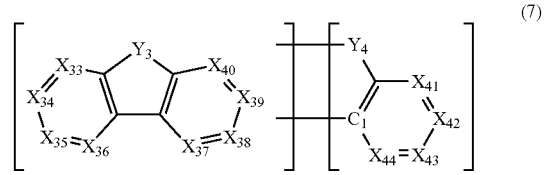

(7)

wherein in the formula (7), $X_{33}$ to $X_{44}$ are independently N (nitrogen atom) or CR$_{14}$ (C is a carbon atom);

R$_{14}$ is a single bond, a hydrogen atom or a substituent and if plural R$_{14}$s are present, the plural R$_{14}$s may be the same or different;

$Y_3$ and $Y_4$ are independently NR$_{15}$, O, S, CR$_{16}$R$_{17}$ or SiR$_{18}$R$_{19}$; R$_{15}$, R$_{16}$, R$_{17}$, R$_{18}$ and R$_{19}$ that may be the same or different, are a single bond, a substituted or unsubstituted alkyl group including 1 to 30 carbon atoms, a substituted or unsubstituted aryl group including 6 to 30 ring carbon atoms or a substituted or unsubstituted heteroaryl group including 5 to 30 ring atoms;

$C_1$ is a carbon atom;

provided that, at least two of $X_{37}$ to $X_{40}$, being adjacent with each other, are both carbon atoms, and one of the two carbon atoms is bonded to $Y_4$ and the other is bonded to $C_1$; and one of R$_{14}$ to R$_{19}$ is a single bond and is bonded to L, provided that if L is a single bond, one of R$_{14}$ to R$_{19}$ is directly bonded to $Z_1$.

2. The heteroarene derivative according to claim 1, wherein $A_1$ and $A_2$ are independently a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted alkoxy group including 1 to 30 carbon atoms, a substituted or unsubstituted aryloxy group including 6 to 30 ring carbon atoms, a substituted or unsubstituted alkylamino group including 1 to 30 carbon atoms or a substituted or unsubstituted arylamino group including 6 to 30 ring carbon atoms.

3. The heteroarene derivative according to claim 1, wherein $A_1$ is a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted alkoxy group including 1 to 30 carbon atoms, a substituted or unsubstituted aryloxy group including 6 to 30 ring carbon atoms, a substituted or unsubstituted alkylamino group including 1 to 30 carbon atoms, a substituted or unsubstituted arylamino group including 6 to 30 ring carbon atoms or a halogen atom.

4. A material for an organic electroluminescence device comprising the heteroarene derivative according to claim 1.

5. An organic electroluminescence device comprising a cathode and an anode and one or more organic thin film layers including an emitting layer between the cathode and the anode, wherein at least one of the organic thin film layers comprises the material for an organic electroluminescence device according to claim 4.

6. The organic electroluminescence device according to claim 5, wherein the emitting layer comprises the material for an organic electroluminescence device.

* * * * *